United States Patent
Davis et al.

(10) Patent No.: US 11,464,781 B2
(45) Date of Patent: Oct. 11, 2022

(54) PDE1 INHIBITORS FOR OPHTHALMIC DISORDERS

(75) Inventors: Robert Davis, San Diego, CA (US); Allen Fienberg, New York, NY (US)

(73) Assignee: INTRA-CELLULAR THERAPIES, INC., New York, NY (US)

(*) Notice: Subject to any disclaimer, the term of this patent is extended or adjusted under 35 U.S.C. 154(b) by 579 days.

(21) Appl. No.: 13/203,365

(22) PCT Filed: Feb. 24, 2010

(86) PCT No.: PCT/US2010/000534
§ 371 (c)(1),
(2), (4) Date: Aug. 25, 2011

(87) PCT Pub. No.: WO2010/098839
PCT Pub. Date: Sep. 2, 2010

(65) Prior Publication Data
US 2011/0312978 A1   Dec. 22, 2011

Related U.S. Application Data

(60) Provisional application No. 61/155,384, filed on Feb. 25, 2009.

(51) Int. Cl.
*A61K 31/535* (2006.01)
*A61K 9/00* (2006.01)
*A61K 31/5575* (2006.01)
*A61P 27/06* (2006.01)

(52) U.S. Cl.
CPC .......... *A61K 31/535* (2013.01); *A61K 9/0048* (2013.01); *A61K 31/5575* (2013.01); *A61P 27/06* (2018.01)

(58) Field of Classification Search
None
See application file for complete search history.

(56) References Cited

U.S. PATENT DOCUMENTS

| | | | |
|---|---|---|---|
| 4,666,908 A | 5/1987 | Hamilton | |
| 5,068,488 A | 11/1991 | Slaugh | |
| 5,079,253 A | 1/1992 | Hoyng et al. | |
| 5,294,612 A | 3/1994 | Bacon et al. | |
| 5,393,755 A | 2/1995 | Neustadt et al. | |
| 5,824,683 A | 10/1998 | McKittrick et al. | |
| 5,849,770 A | 12/1998 | Head et al. | |
| 5,939,419 A | 8/1999 | Tulshian | |
| 5,962,492 A | 10/1999 | Warrellow et al. | |
| 6,013,621 A | 1/2000 | Nishi et al. | |
| 6,133,273 A | 10/2000 | Gilbert et al. | |
| 6,235,742 B1* | 5/2001 | Bell et al. ................ | 514/249 |
| 6,235,746 B1 | 5/2001 | Davis et al. | |
| 6,316,444 B1 | 11/2001 | Hunt et al. | |
| 6,333,354 B1 | 12/2001 | Schudt | |
| 6,423,716 B1 | 7/2002 | Matsuno et al. | |
| 6,492,371 B2 | 12/2002 | Roylance | |
| 6,498,165 B1 | 12/2002 | Armstrong et al. | |
| 6,552,029 B1 | 4/2003 | Davis et al. | |
| 6,586,423 B2 | 7/2003 | Bilodeau et al. | |
| 6,599,908 B1 | 7/2003 | Davis et al. | |
| 6,649,608 B2 | 11/2003 | Pease et al. | |
| 6,670,368 B1 | 12/2003 | Breault et al. | |
| 6,693,099 B2 | 2/2004 | Degenhardt et al. | |
| 6,756,373 B1 | 6/2004 | Allerton et al. | |
| 6,943,171 B2 | 9/2005 | Asberom et al. | |
| 6,969,719 B2 | 11/2005 | Asberom et al. | |
| 7,153,824 B2 | 12/2006 | Palmer et al. | |
| 8,273,750 B2 | 9/2012 | Li et al. | |
| 8,273,751 B2 | 9/2012 | Li et al. | |
| 8,536,159 B2 | 9/2013 | Li et al. | |
| 8,633,180 B2 | 1/2014 | Li et al. | |
| 8,664,207 B2* | 3/2014 | Li et al. ................ | 514/171 |
| 8,697,710 B2 | 4/2014 | Li et al. | |
| 9,849,132 B2* | 12/2017 | Hendrick ............... | A61K 31/53 |
| 2003/0069246 A1 | 4/2003 | Darrow et al. | |
| 2003/0162782 A1 | 8/2003 | Grossman et al. | |
| 2004/0087479 A1* | 5/2004 | Sosnowski et al. .............. | 514/1 |
| 2004/0087517 A1 | 5/2004 | Burnet et al. | |
| 2004/0137068 A1* | 7/2004 | Bhushan ...................... | 424/486 |
| 2004/0259792 A1 | 12/2004 | Palmer et al. | |

(Continued)

FOREIGN PATENT DOCUMENTS

| | | |
|---|---|---|
| DE | 19931206 A1 | 1/2001 |
| EP | 0063381 | 10/1982 |

(Continued)

OTHER PUBLICATIONS

Gupta et al., Glaucoma as a neurodegenerative disease, Curr Opin Ophthalmol. Mar. 2007;18(2):110-4, printed from http://www.ncbi.nlm.nih.gov/pubmed/17301611, abstract only, 1 page.*
Orzalesi et al., Comparison of the effects of latanoprost, travoprost, and bimatoprost on circadian intraocular pressure in patients with glaucoma or ocular hypertension, Ophthalmology. Feb. 2006;113(2):239-46, printed from https://www.ncbi.nlm.nih.gov/pubmed/16458092, Abstract only, 2 pages.*
U.S. Pharmacist, How to Use Eye Drops Properly, Mar. 14, 2003, printed from https://www.uspharmacist.com/article/how-to-use-eye-drops-properly, 2 pages.*
U.S. Appl. No. 14/252,511, filed Apr. 14, 2014, Li et al.
Actions issued in U.S. Pat. No. 8,273,750, dated Sep. 13, 2012, Aug. 24, 2012, Jul. 23, 2012, Apr. 18, 2012, Jan. 31, 2012, Aug. 16, 2011, Mar. 30, 2010, Dec. 30, 2009, Aug. 18, 2009.
Actions issued in U.S. Pat. No. 8,273,751, dated Apr. 26, 2012, Mar. 27, 2012, Nov. 29, 2011.
Actions issued in U.S. Appl. No. 13/486,264, dated Jan. 14, 2014, Oct. 24, 2013, Apr. 30, 2013.
"Anxiety," [retrieved on May 14, 2008]. Retrieved online via Internet, URL: http://www.nim.nih.gov/medlineplus/anxiety.html, 5 Pages.

(Continued)

*Primary Examiner* — Gigi G Huang
(74) *Attorney, Agent, or Firm* — Hoxie & Associates LLC

(57) ABSTRACT

Compounds that inhibit phosphodiesterase 1 (PDE1) are useful to treat glaucoma or elevated intraocular pressure. The PDE1 inhibitors may be administered as monotherapy or in combination with additional intraocular-pressure lowering agents. In addition, the invention provides ophthalmic compositions comprising PDE 1 inhibitors and optionally one or more additional intraocular pressure-lowering agents. Topical and systemic therapy may be used.

6 Claims, No Drawings

(56) References Cited

U.S. PATENT DOCUMENTS

| | | |
|---|---|---|
| 2005/0075795 A1 | 4/2005 | Pandit |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2008/0275054 A1 | 11/2008 | Holzer et al. |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0273754 A1 | 10/2010 | Li et al. |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li et al. |
| 2012/0238589 A1 | 9/2012 | Li et al. |
| 2013/0018063 A1 | 1/2013 | Li et al. |
| 2013/0239234 A1 | 9/2013 | Greengard et al. |
| 2013/0085123 A1 | 12/2013 | Li et al. |
| 2013/0324565 A1 | 12/2013 | Li et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |

FOREIGN PATENT DOCUMENTS

| | | |
|---|---|---|
| EP | 0201188 | 12/1986 |
| EP | 0583821 | 2/1994 |
| EP | 0911333 | 4/2002 |
| JP | 53031694 | 3/1978 |
| WO | WO 1988/005306 | 7/1988 |
| WO | WO 1988/007380 | 10/1988 |
| WO | WO 1991/019717 | 12/1991 |
| WO | WO 1994/019351 | 9/1994 |
| WO | WO 1998/046606 | 10/1998 |
| WO | WO 1998/052568 | 11/1998 |
| WO | WO 2003/002567 | 1/2003 |
| WO | WO 2003/020702 | 3/2003 |
| WO | WO 2003/020724 | 3/2003 |
| WO | WO 2003/042216 | 5/2003 |
| WO | WO 2003/066030 | 10/2003 |
| WO | WO 2006/133261 | 12/2006 |
| WO | WO 2006133261 A2 * | 12/2006 |
| WO | WO 2007/143568 | 12/2007 |
| WO | WO 2007/143705 | 12/2007 |
| WO | WO 2009/073210 | 6/2009 |
| WO | WO 2010/065147 | 6/2010 |
| WO | WO 2010/065148 | 6/2010 |
| WO | WO 2010/065149 | 6/2010 |
| WO | WO 2010/065151 | 6/2010 |
| WO | WO 2010/065152 | 6/2010 |
| WO | WO 2010/065153 | 6/2010 |
| WO | WO 2013/192556 | 12/2013 |

OTHER PUBLICATIONS

"Autism," [retrieved on May 14, 2008]. Retrieved online via Internet, URL: http://www.nim.nih.gov/medlineplus/autism.html, 6 pages.

Ahn, H., et al. "Potent Tetracyclic Guanine Inhibitors of PDE1 and PDE5 Cyclic Guanosine Monophosphate Phosphodiesterases with Oral Antihypertensive Activity", J. Med. Chem. (1997) 40(14):2196-2210.

Al-Afaleq, E., et al., "Heterocyclic o-Aminonitriles: Preparation of Pyrazolo[3,4-d]-pyrimidines with Modification of the substituents at the 1-position", Molecules, 6, pp. 621-638, (2001).

Al-Saikhan, F., "The Gene Therapy Revolution in Ophthalmology", Saudi Journal of Ophthalmology (2013) 27, 107-111.

Aswar, "Anti-Cataleptic Activity of Various Extracts of Ocimum Sanctum", International Journal of Pharma. Research and Development, vol. 2, Issue 6, pp. 1-7 (2010).

Banker, Gilbert S. et al., Modern Pharmaceutics, Marcel Dekker, New York, 1996, pp. 451 and 596 only.

Bastia et al., Effect of $A_1$ and $A_{2A}$ Adenosine Receptor Ligands in Mouse Acute Models of Pain, Neuroscience letters (2002) 328:241-244.

Bender et al., "Cyclic Nucleotide Phosphodiesterases: Molecular Regulation to Clinical Use" PharmcoL Rev., 2006, 58, pp. 488-520.

Blokland, "PDE Inhibition and Cognition Enhancement", vol. 22 No. 4, pp. 349-354 (2012) (Abstract Only).

Boyd et al., "Dopamine receptor signaling and current and future antipsychotic drugs", Handb Exp Pharmacol. 2012; (212):53-86. DOI: 10.1007/978-3-642-25761-2_3.

Burnouf et al., "Synthesis, Structure-Activity Relationships, and Pharmacological Profile of 9-Amino-4-Oxo-1-Phenyl-3,4,5,6,7-Tetrahydrol[1,4]Diazepino[6, 7, 1-hi]lndoles: Discovery of Potent, Selective Phosphodiesterase Type 4 Inhibitors," (2000), J. Med. Chem., 43:4850-4867.

Cantrill, H.L., et al., "The Effects of Theophylline on cyclic adenosine monophosphate metabolism in lymphocytes from open-angle glaucoma patients", Investigative Ophthalmology, vol. 13, No. 9, (1974), pp. 688-691.

Chalimoniuk "Upregulation of guanylyl cyclase expression and activity in striatum of MPTP-induced parkinsonism in mice" Biochem. Biophys. Res Commun. Nov. 5, 2004;324(1):118-26.

Chebib et al., 1-Phenylpyrazolo[3,4-d]pyrimidines; Structure-Activity Relationships for C6 Substituents at $A_1$ and $A_{2A}$ Adenosine Receptors Bioorganic & Medicinal Chemistry (2000) 8:2581-2590.

Chen et al., Effects of Bimatoprost 0.03% on Ocular Hemodynamics in Normal Tension Glaucoma; Journal of Ocular Pharmacology and Therapeutics, vol. 22, No. 3, 2006.

Chen, L. et al., "Hydrostatic pressure-dependent changes in cyclic AMP signaling in optic nerve head astrocytes from Caucasian and African American Donors", Molecular Vision, (2009), 15:1664-1672.

Davis, R. J., et al., "Functional Rescue of Degenerating Photoreceptors in Mice Homozygous for a Hypomorphic cGMP Phosphodiesterase 6 b Allele ($Pde6b^{H620Q}$)", Invest Ophthalmol Vis. Sci., 2008, 49(11) 5067-5076, DOI:10.1167/iovs.07-1422.

Davis, R. J., et al., "Therapeutic Margins in a Novel Preclinical Model of Retinitis Pigmentosa", The Journal of Neuroscience, 2013, 33(33), pp. 13475-13483.

Deshmukh et al., "Amelioration of intracerebroventricular streptozotocin induced cognitive dysfunction and oxidative stress by vinpocetine—a PDE1 inhibitor" European Journal of Pharmacology (2009), 620(1-3), 49-56.

Dewald et al., Synthesis and Potential Antipsychotic Activity of 1 H-Imidazo[1.2-c]pyrazolo[3,4-e]pyrimidines, J. Med. Chem. 1988, 31, pp. 454-461.

Dong, C., et al., α2 Adrenergic Modulation of NMDA Receptor Function as a Major Mechanism of RGC Protection in Experimental Glaucoma and Retinal Excitotoxicity, Investigative Ophthalmology & Visual Science, 2008, vol. 49, No. 10, pp. 4515-4522.

Ehrman et al., "Phosphodiesterase 1B differentially modulates the effects of methamphetamine on locomotor activity and spatial learning through DARPP32-dependent pathways: evidence from PDE1B-DARPP32 double-knockout mice", Genes Brain Behav. Oct. 2006;5(7):540-51.

Fienberg et al., "DARPP-32: Regulator of the Efficacy of Dopaminergic Neurotransmission", Science, (1998) 281, pp. 838-842.

Filgueiras et al., "Phosphodiesterase type 1 inhibition improves learning in rats exposed to alcohol during the third trimester equivalent of human gestation" Neuroscience Letters (2010), 473(3), 202-207.

Gani, J., et al., "Urologic Medications and Ophthalmologic Side Effects: A Review", Can Urol Assoc J 2012; 6(1):53-8. http://dx.doi.org/10.5489/cuaj.11037.

(56) References Cited

OTHER PUBLICATIONS

Gelbin, et al., "Ketene-S, N-acetals as synthons for heterocycles new synthesis of pyrimidinones", Journal Fuer Praktische Chemie, vol. 329, No. 5, pp. 753-766, (1987).

Greengard et al., "Beyond the Dopamine Receptor: the DARPP-32 IProtein Phosphatase-1 Cascade", Neuron, 1999,23, pp. 435,447.

Grigorvera, E., "A Differentiated Approach to the Treatment of Normal-Pressure Glaucoma", Vestn Oftalmol. Sep.-Oct. 2003;119(5):14-6. (English Abstract Only).

Han et al., "The Calcium/Calmodulin-dependent Phosphodiesterase PDE1C Downregulates Glucose-induced Insulin Secretion", J. Bio. Chem., 1999,274(32), pp. 22337-22344.

Hasegawa, Y., et al., Prostaglandin F2α, but Not Latanoprost, Increases the Ca$^{2+}$ Sensitivity of the Pig Iris Sphincter Muscle, Investigative Ophthalmology & Visual Science, 2006, vol. 47, No. 11, pp. 4865-4871.

Hulley et al., "Cyclic AMP promotes the survival of dopaminergic neurons in vitro and protects them from the toxic effects of MPP+" J Neural Transm Suppl. (1995); 46:217-28.

Husain, S., et al., "Alterations in Arachidonic Acid Release and Phospholipase C-β1 Expression in Glaucomatous Human Ciliary Muscle Cells", Investigative Ophthalmology & Visual Science, Apr. 2002, vol. 43, No. 4, pp. 1127-1134.

Husain, S., et al., "Mechanisms Linking Adenosine A1 Receptors and Extracellular Signal-Regulated Kinase 1/2 Activation in Human Trabecular Meshwork Cells", The Journal of Pharmacology and Experimental Therapeutics, vol. 320, No. 1, 2007, pp. 258-265.

Iyer, P., "Autotaxin-Lysophosphatidic Acid Axis is a Novel Molecular Target for Lowering Intraocular Pressure", PLoS ONE, 2012, 7(8): e42627, DOI:10.1371/journal.pone.0042627.

Janisch, K. M., Light-dependent phosphorylation of the gamma subunit of cGMP-Phophodiesterase (PDE6γ) at residue threonine 22 in intact photoreceptor neurons, Biochem Biophys Res Commun. 2009; 390(4): 1149-1153. DOI:10.1016/j.bbrc.2009.10.106.

Jiang, et al., "Chemoenzymatic Asymmetric Total Synthesis of Phosphodiesterase Inhibitors: Preparation of a Polycyclic Pyrazolo[3,4-d]pyrimidine from an Acylnitroso Oiels-Alder Cycloadduct-Derived Aminocyclopentenol", J. Org. Chem., 70, 2824-2827 (2004).

Jones, B.W., et al., "Retinal Remodeling", Jpn J Ophthalmol. 2012; 56(4): 289-306. DOI:10.1007/s10384-012-0147-2.

Kakkar, et al. "Amantadine: an antiparkinsonian agent inhibits bovine brain 60 kDa calmodulin-dependent cyclic nucleotide phosphodiesterase isozyme", Brain Res. Feb. 28, 1997;749(2):290-4.

Kakkar, et al. "Calmodulin-dependent cyclic nucleotide phosphodiesterase (PDE1)" Cell Mol Life Sci. Jul. 1999;55(8-9):1164-86.

Kakkar, et al., "Inhibition of Bovine Brain Calmodulin-Dependent Cyclic Nucleotide Phosphodiesterase Isozymes by Deprenyl", Life Sciences, vol. 59, No. 21, pp. 337-341 (1996).

Klaissle, "Physical activity and environmental enrichment regulate the generation of neural precursors in the adult mouse substantia nigra in a dopamine-dependent manner" BMC Neurosci. 2012)31;13:132. doi: 10.1186/1471-2202-13-132.

Kleppisch, "Phosphodiesterases in the central nervous system" Handb Exp Pharmacol. 2009;(191):71-92. DOI: 10.1007/978-3-540-68964-5_5.

Koksal, M., et al., "The Effects of Sildenafil on Ocular Blood Flow", Acta Ophthalmol. Scand. 2005: 83: 355-359, DOI: 10.1111/j.1600-0420.2004.00422.x.

Laddha et al., "A new therapeutic approach in Parkinson's disease: Some novel quinazoline derivatives as dual selective phosphodiesterase 1 inhibitors and anti-inflammatory agents" Bioorganic & Medicinal Chemistry (2009), 17(19), 6796-6802.

Lundqvist et al., "Exploitation of Structural and Regulatory Diversity in Glutamate Racemases", Nature (2007) 447:817-822.

Mani et al., "Requirement for DARPP-32 in Progesterone-Facilitated Sexual Receptivity in Female Rats and Mice", Science (2000) 287: 1053.

Medina. "Therapeutic Utility of Phosphodiesterase Type 1 Inhibitors in Neurological Conditions", Front. Neurosci. 5: 21, 6 pages, (2011).

Murray et al., "Expression and activity of cAMP phosphodiesterase isoforms in pulmonary artery smooth muscle cells from patients with pulmonary hypertension: role for PDE1", Am. J. Physiol. Lunr:l Cell Mol. Physiol. 2007, 292, pp. L294-L303.

Murray et al., "LY503430, a Novel_-Amlno-3-hydroxy-5-methylisoxazole-4-proplonlc Acid Receptor Potentiator with Functional, Neuroprotective and Neurotrophic Effects in Rodent Models of Parkinson's Disease" JPEJ (2003) 306:752-762.

Nishi, A., et al., "Advanced Research on Dopamine Signaling to Develop Drugs for the Treatment of Mental Disorders: Biochemical and Behavioral Profiles of Phosphodiesterase Inhibition in Dopaminergic Neurotransmission", J. Pharmacol. Sci. vol. 114, pp. 6-16, (2010).

Noguchi et al., "A Facile Preparation of 7-(substituted amino-)-6H-pyrrolo[3,4-d]-pyrimidine Derivatives"; Bulletin Chem. Soc. of Japan, 1989, 62(9), 3043-5.

Park, et al., "Traumatic Brain Injury: Can the consequences be stopped?" CMAJ, 178(9), 1163-1170, (2008).

Pelletier, A.L., et al, "Vision Loss in Older Persons", American Family Physician, vol. 79, No. 11, 963-970, (2009).

Pemp, B., et al., "The effects of moxaverine on ocular blood flow in patients with age-related macular degeneration or primary open angle glaucoma and in healthy control subjects", Acta Ophthalmol. 2012: 90: 139-145, DOI: 10.1111/j.1755-3768.2010.01878.x.

Polli et al., "Expression of a Calmodulin-Dependent Phosphodiesterase Isoform (PDE1 B1) Correlates With Brain Regions Having Extensive Dopaminergic Innervation," (1994), The Journal of Neuroscience, 14:1251-1261.

Porsolt et al. Nature (1977) 266:730-732.

Poulsen et al., High-Pressure Synthesis of Enantiomerically Pure C-6 Substituted Pyrazolo[3,4-d]pyrimidines Biorganic & Medicinal Chemistry letter (2001) 11:191-193.

Ramasamy, B., et al., "Acute angle-closure glaucoma following sildenafil citrate-aided sexual intercourse", Acta Ophthalmologica Scandinavica 2007, p. 229, DOI:10.1111/j.1600-0420.2006.00803.x.

Reed et al., "Phosphodiesterase 1 B Knock-Out Mice Exhibit Exaggerated Locomotor Hyperactivity and DARPP-32 Phosphorylation in Response to Dopamine Agonists and Display Impaired Spatial Learning", The Journal of Neuroscience, 2002, 22(12), pp. 5188-5197.

Reingardiene, D., "Beta-adrenergic receptor blocker poisoning", Medicina (Kaunas). 2007;43(7):587-93. (English Abstract Only).

Rybalkin et al., "Cyclic GMP Phosphodiesterases and Regulation of Smooth Muscle Function", Circ. Res. 2003, 93, pp. 280-291.

Schmidt, "Phosphodiesterase inhibitors as potential cognition enhancing agents" Current Topics in Medicinal Chemistry (2010), 10(2), 222-230.

Sharma, et al., "Regulation of Calmodulin-Stimulated Cyclic Nucleotide Phosphodiesterase (PDE1): Review", International Journal of Molecular Medicine, 18: 95-105 (2006).

Shimizu et al., "Calmodulin-Dependent Cyclic Nucleotide Phosphodiesterase (PDE1) is a Pharmacological Target of Differentiation-Inducing Factor-1, an Antitumor Agent Isolated from Dictyostelium", Cancer Research, 2004, 64, pp. 2568-2571.

Shook, et al. "Design and Characterization of Optimized Adenoside A$_{2A}$/A$_1$ Receptor Antagonists for the Treatment of Parkinson's Disease", J. Med. Chem., pp. 1-47 (2012).

Tosi, J., et al., "shRNA knockdown of Gucy2e or Cnga1 increases photoreceptor survival in a cGMP phosphodiesterase mouse model of retinitis pigmentosa", J Cell Mol Med. 2011; 15(8): 1778-1787. DOI:10.1111/j.1582-4934.2010.01201.x.

Tsang, S.H., et al., "A novel mutation and phenotypes in phosphodiesterase 6 deficiency", Am J Ophthalmol. 2008; 146(5): 780-788. DOI:10.1016/j.ajo.2008.06.017.

Tsang, S.H., et al., "Function of the asparagine 74 residue of the inhibitory γ-subunit of retinal rod cGMP-phophodiesterase (PDE) in vivo", Cell Signal. 2011; 23(10): 1584-1589. DOI:10.1016/j.cellsig.2011.05.007.

Tsang, S.H., et al., "Transgenic Mice Carrying the H258N Mutation in the Gene Encoding the β-Subunit of Phosphodiesterase-6 (PDE6B)

(56) References Cited

OTHER PUBLICATIONS

Provide a Model for Human Congenital Stationary Night Blindness", Hum Mutat. 2007; 28(3): 243-254. DOI:10.1002/humu.20425.

Tsang, S.H., et al., "Removal of phosphorylation sites of γ subunit of phosphodiesterase6 alters rod light response", J Physiol 579.2 (2007) pp. 303-312, DOI: 10.1113/jphysiol.2006.121772.

Turko et al., "Inhibition of Cyclic GMP-Binding Cyclic GMP-Specific Phosphodiesterase (Type 5) by Sildenafil and Related Compounds", Molecular Pharmacology (1990) 56:124-130.

UNGERSTEDT Acta Physiology Second Suppl. (1971) 367:1-48.

Ungerstedt et al. Brain Research (1970) 24: 485-493.

Vatter, et al., "Differential Phosphodiesterase Expression and Cytosolic Ca2+ in Human CNS Tumour Cells and in Non-Malignant and Malignant Cells of Rat Origin", J. of Neurochemistry, 93, 321-329 (2005).

Wert, K.J., "Gene therapy provides long-term visual function in a pre-clinical model of retinitis pigmentosa", Human Molecular Genetics, 2013, vol. 22, No. 3, 558-567, DOI:10.1093/hmg/dds466.

Wolff, M.E., Burger's Medicinal Chemistry and Drug Discovery, Fifth Ed., vol. 1: Principles and Practice, John Wiley & Sons, 1995, 975.

Xia, et al., "Synthesis and Evaluation of Polycyclic Pyrazolo[3,4-d]pyrimidines as PDE1 and PDE5 cGMP Phosphodiesterase Inhibitors", J. Med. Chem., 40, 4372-77 (1997).

Zhou, B.L., "Single nucleotide polymorphisms of metabolic syndrome-related genes in primary open angle glaucoma", Int. J. Ophthalmol, vol. 3, No. 1, 2010, pp. 36-42, DOI:10.3980/j.issn.2222-3959.2010.01.09.

Beringer, P. et al., Eds., Remington: The Science and Practice of Pharmacy, 21st Edition, Lippincott Williams & Wilkins, Philadelphia, 2006, Chapter 43, pp. 856-863.

Chermat et al. Journal Pharmacology (1986) 17: 348-350.

Goodman & Gilman, The Pharmacological Basis of Therapeutics, McGraw-Hill Interamericana. 2007, p. 892 (cited within text of Office Action from corresponding Costa Rican application, attached herein).

Okamoto, N., et al., "Preparation of Ophthalmic Formulations Containing Cilostazol as an Anti-glaucoma Agent and Improvement in Its Permeability through the Rabbit Cornea", J. Oleo Sci., 59, (8) 423-430 (2010).

\* cited by examiner

PDE1 INHIBITORS FOR OPHTHALMIC DISORDERS

CROSS-REFERENCE TO RELATED APPLICATIONS

This application is a United States Application under 35 USC § 371 claiming benefit of PCT/US2010/000534 filed Feb. 24, 2010, which claims the benefit of U.S. Application Ser. No. 61/155,384 filed on Feb. 25, 2009, the contents of each of which are herein incorporated by reference.

FIELD OF THE INVENTION

The field relates to inhibitors of phosphodiesterase 1 (PDE1) for treatment of ophthalmic disorders, e.g., topical or systemic treatment of glaucoma or elevated intraocular pressure, and to ophthalmic formulations of PDE1 inhibitors.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), which are activated by the $Ca^{2+}$-calmodulin and have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases downregulate intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 inhibits the activity of protein phosphatase-1 (PP-1), which helps maintain the state of phosphorylation of many PP-1 substrate proteins, e.g., alpha-amino-3-hydroxy-5-methylisoxazole-4-propionic acid (AMPA) receptor subunit, leading to the induction of physiological responses. PDE1 inhibitors are therefore potentially useful in diseases characterized by abberant dopamine or calcium-calmodulin signaling activity.

EP 0201188 and EP 0911333, the contents of which are incorporated herein by reference, disclose certain 1,3,5,-substituted, 6,7-dihydro-1H-pyrazolo[4,3-d]pyrimidin-7-one compounds. PCT/US2006/33179, the contents of which are incorporated herein by reference, discloses the use of 1,3,5,-substituted, 6,7-dihydro-1H-pyrazolo[4,3-d]pyrimidin-7-one compounds for treatment of diseases involving disorders of the dopamine D1 receptor intracellular pathway, but does not specifically disclose the use of such compounds in the treatment or management of glaucoma PCT/US2006/022066, the contents of which are incorporated herein by reference, discloses PDE1 inhibitors which are 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, but does not specifically disclose their use for the enhancement of progesterone signaling. WO 03/042216, U.S. Pat. No. 5,939,419, EP 0 538 332, U.S. Pat. Nos. 5,393,755, 6,969,719 B2, Xia et al., *J. Med. Chem.* (1997), 40, 4372-4377 and Ahn et al., *J. Med. Chem.* (1997), 40, 2196-2210, the contents of which are incorporated herein by reference, disclose PDE1/PDE5 cGMP phosphodiesterase inhibitors which are substituted pyrazolo[3,4-d]pyrimidine or imidazo[2,1-b]purin-4-one analogues useful for the treatment of hypertensive, cardiovascular, sexual dysfunction and other cGMP-PDEV related disorders, but do not specifically disclose their use for treatment or management of glaucoma.

Glaucoma is an eye disorder characterized by increased intraocular pressure, cupping of the optic disc, and visual field loss. Although the pathophysiological mechanism of open angle glaucoma is still unknown, there is substantial evidence to suggest that increased intraocular pressure is detrimental to the eye, and that the increased intraocular pressure in glaucoma is the most important factor causing degenerative changes in the retina. In one particular form of glaucoma, low tension glaucoma, the actual situation may simply be that the eye is unusually sensitive to pressure and therefore damage may occur at intraocular pressure levels otherwise regarded as physiologically normal.

On the other hand, some individuals may exhibit an abnormally high intraocular pressure substantially without any manifest defects in the visual field or optic disc. Such individuals are referred to as ocular hypertensives. If untreated, glaucoma almost invariably leads to blindness. The course of the disease typically is slow with progressive loss of vision. The basic principle of glaucoma treatment is to lower the intraocular pressure, either by drugs, laser treatment or surgery. The modality of treatment with drugs comprises typically instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g., 1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.

3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (parasympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

Although with many of these drugs, the positive effects obtained are at least appreciable, concomitant adverse side-effects are often encountered which tend to diminish the usefulness of the drugs and may negatively affect patient compliance. For example prostanoids use has been reported to be associated with exacerbation of uveitis and cystoid macular edema. Of some concern is the ability of these agents to cause permanent iris color changes. Blue/green iris color may become brownish. Improvements in these respects are desirable, as well as improvements in drug efficacy. Further, alpha adrenergic agonists use is associated with side effects including conjunctival hyperemia (the eye appears red) along with conjunctival follicle formation. Severe hypotension and other cardiovascular side effects have been reported in infants and toddlers with alpha agonists.

Use of nonselective PDE inhibitors in combination with IOP lowering agents was suggested some years ago, e.g., in EP 0583821 and U.S. Pat. No. 5,079,253. However, nonselective PDE inhibitors may presents risks of side effects and may even interfere with normal ocular function, altering function in photoreceptive cells. For whatever reason, nonselective PDE inhibitors have not been further developed for this purpose. There is a need for methods of treatment that can effectively treat glaucoma without interfering with normal ocular function or presenting unacceptable side effects.

SUMMARY OF THE INVENTION

The invention provides a new method of treatment or prophylaxis of glaucoma, or elevated intraocular pressure that may be ameliorated by administration of a specific inhibitor of phosphodiesterase type I (PDE1 inhibitor).

In one embodiment, the invention provides a method of treatment for glaucoma or elevated intraocular pressure comprising administration of an effective amount of a PDE1 inhibitor to a patient in need thereof.

For example, the invention provides a method of treatment for glaucoma or elevated intraocular pressure comprising topical administration of a therapeutically effective amount of a phospodiesterase type I inhibitor (PDE1 inhibitor) in an opthalmically compatible carrier to the eye of a patient in need thereof. However, treatment may alternatively include a systemic therapy. Systemic therapy includes treatment that can directly reach the bloodstream, or oral methods of administration, for example.

The invention further provides a pharmaceutical composition for topical ophthalmic use comprising a PDE1 inhibitor; for example an ophthalmic solution, suspension, cream or ointment comprising a PDE1 inhibitor, e.g., as hereinafter described, in free or ophthamalogically acceptable salt form, in combination or association with an ophthamologically acceptable diluent or carrier.

Optionally, the PDE1 inhibitor may be administered sequentially or simultaneously with a second drug useful for treatment of glaucoma or elevated intraocular pressure. Where two active agents are administered, the therapeutically effective amount of each agent may be below the amount needed for activity as monotherapy. Accordingly, a subthreshold amount (i.e., an amount below the level necessary for efficacy as monotherapy) may be considered therapeutically effective and also may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a subthreshold amount, of a PDE1 inhibitor, such that amount of the agent known to lower intraocular pressure and the amount of the PDE1 inhibitor in combination are effective to treat the condition. In one embodiment, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 inhibitor. However, methods other than topical administration, such as systemic therapeutic administration, may also be utilized.

In a further embodiment, the invention provides a method of lengthening or enhancing growth of the eyelashes by administering an effective amount of a prostaglandin analogue, e.g., bimatoprost, concomitantly, simultaneously or sequentially with an effective amount of a PDE1 inhibitor, to the eye of a patient in need thereof.

The invention further provides a pharmaceutical composition for topical ophthalmic use comprising a PDE1 inhibitor and an agent known to reduce intraocular pressure.

The PDE1 inhibitor is optionally selected from the PDE1 inhibitors as hereinafter described. For example, the PDE1 inhibitor may be selected from 7,8-dihydro-[1Hor 2H]-imidazo[1,2-α]pyrazolo[4,3-e]pyrimidin-4(5H)-ones or 7,8,9-trihydro-[1Hor 2H]-pyrimido[1,2-a]pyrazolo[4,3-e]pyrimidin-4(5H)-ones, substituted at the 1 or 2 position with $C_{2-9}$ alkyl or $C_{3-9}$ cycloalkyl, or optionally substituted heteroarylalkyl or substituted arylalkyl, in free, salt or prodrug form (hereinafter a PDE 1 Inhibitor, e.g., as described below) or a 1,3,5-substituted 6,7-dihydro-1H-pyrazolo[4,3-i/]pyrimidin-7-one, in free, salt or prodrug form; or substituted imidazo[2,1-b]purin-4-one, e.g., (6aR,9aS)-2(biphenyl-4-ylmethyl)-5,6a,7,8,9,9a-hexahydro-5-methyl-3(phenylmethyl)-cyclopent-[4,5]imidazo-[2,1-b]purin-4(3H)-one, (6aR,9aS)-5,6a,7,8,9,9a-hexahydro-5-methyl-2,3-bis(phenylmethyl)cyclopent-[4,5]imidazo-[2,1-b]purin-4(3H)-one, 5'-methyl-2',3'-bis(phenylmethyl)spiro[cyclopentane-1,7'(8H)-[3H]imidazo[2,1-b]purin]-4'(5'H)-one, or 5'-methyl-2'-(biphenyl-4-ylmethyl)-3'-(phenylmethyl)spiro[cyclopentane-1,7'

(8'H)[3H]imidazo[2,1-b]purin]-4'(5'H)-one; or other compounds which selectively inhibit phosphodiesterase 1 (PDE1) activity, especially PDE1B activity, and so are useful for the treatment of glaucoma or elevated intraocular pressure.

The optional additional agent or agents for use in combination with a PDE1 inhibitor may, for example, be selected from the existing drugs described in paragraph 8, supra. For example, the invention provides pharmaceutical compositions comprising a PDE1 inhibitor and an agent selected from (i) the prostanoids, unoprostone, latanoprost, travoprost, or bimatoprost; (ii) an alpha adrenergic agonist such as brimonidine, apraclonidine, or dipivefrin and (iii) a muscarinic agonist, such as pilocarpine. For example, the invention provides ophthalmic formulations comprising a PDE-1 inhibitor together with bimatoprost, abrimonidine, brimonidine, timolol, or combinations thereof, in free or ophthamalogically acceptable salt form, in combination or association with an ophthamologically acceptable diluent or carrier. However, in addition to selecting a combination, a person of ordinary skill in the art can select an appropriate selective receptor subtype agonist or antagonist. For example, for alpha adrenergic agonist, one can select an agonist selective for an alpha 1 adrenergic receptor, or an agonist selective for an alpha$_2$ adrenergic receptor such as brimonidine, for example. For a beta-adrenergic receptor antagonist, one can select an antagonist selective for either $\beta_1$, or $\beta_2$, or $\beta_3$, depending on the appropriate therapeutic application. One can also select a muscarinic agonist selective for a particular receptor subtype such as $M_1$-$M_5$.

The PDE 1 inhibitor may be administered in the form of an ophthalmic composition, which includes an ophthalmic solution, cream or ointment. The ophthalmic composition may additionally include an intraocular-pressure lowering agent.

In yet another example, the PDE-1 inhibitors disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

DETAILED DESCRIPTION OF THE INVENTION

Compounds for Use in the Methods of the Invention

The examples described and drawings rendered are illustrative and are not to be read as limiting any claim scope or claim construction.

In one example, the PDE 1 Inhibitors for use in the methods of treatment described herein are a 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, of formula I:

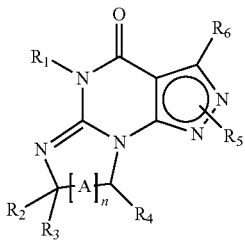

Formula I wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl
or
$R_5$ is attached to one of the nitrogens on the pyrazolo portion of Formula I and is a moiety of Formula Q

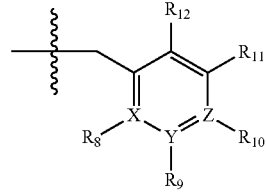

Formula Q wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and
(iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and
(v) n=0 or 1;
(vi) when n=1, A is —C($R_{13}R_{14}$)—
wherein $R_{13}$ and $R_{14}$, are, independently, H or $C_{1-4}$ alkyl, aryl, heteroaryl, (optionally hetero)arylalkoxy or (optionally hetero)arylalkyl;
in free, salt or prodrug form, including its enatiomers, diasterisomers and racemates.

The invention further provides the use of PDE 1 Inhibitors of Formula I as follows:

1.1 Formula I wherein $R_1$ is methyl and n=0;
1.2 Formula I or 1.1 wherein $R_4$ is H or $C_{1-4}$ alkyl and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;
1.3 Formula I or 1.1 wherein $R_4$ is H and at least one of $R_2$ and $R_3$ is arylalkoxy;
1.4 Formula I wherein $R_1$ is methyl, $R_2$, $R_3$, and $R_4$ are H, n=1, and $R_{13}$ and $R_{14}$ are, independently, H or $C_{1-4}$ alkyl (e.g., methyl or isopropyl);
1.5 Formula I or 1.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;

1.6 Formula I, 1.1 or 1.5 wherein $R_5$ is a substituted heteroarylmethyl, e.g., para-substituted with haloalkyl;

1.7 Formula I, 1.1, 1.2, 1.3, 1.4 or 1.5 wherein $R_5$ is a moiety of Formula Q wherein $R_8$, $R_9$, $R_{11}$, and $R_{12}$ are H and $R_{10}$ is phenyl;

1.8 Formula I, 1.1, 1.2, 1.3, 1.4 or 1.5 wherein $R_5$ is a moiety of Formula Q wherein $R_8$, $R_9$, $R_{11}$, and $R_{12}$ are H and $R_{10}$ is pyridyl or thiadiazolyl;

1.9 Formula I, 1.1, 1.2, 1.3, 1.4 or 1.5 wherein $R_5$ is a moiety of Formula Q wherein $R_8$, $R_9$, $R_{11}$, and $R_{12}$ are, independently, H or halogen, and $R_{10}$ is haloalkyl;

1.10 Formula I, 1.1, 1.2, 1.3, 1.4 or 1.5 wherein $R_5$ is a moiety of Formula Q wherein $R_8$, $R_9$, $R_{11}$, and $R_{12}$ are, independently, H, and $R_{10}$ is alkyl sulfonyl;

1.11 any of the preceding formulae wherein $R_5$ is attached to the 2-position nitrogen on the pyrazolo ring;

1.12 any of the preceding formulae wherein $R_6$ is benzyl;

1.13 any of the preceding formulae wherein $R_6$ is phenylamino or phenylalkylamino (e.g., benzylamino);

1.14 any of the preceding formulae wherein $R_6$ is phenylamino;

1.15 any of the preceding formulae wherein X, Y, and Z are all C;

1.16 any of the preceding formulae wherein X, Y, and Z are all C and $R_{10}$ is phenyl or 2-pyridyl; and/or 1.17 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1;

in free or salt form.

For example, the PDE 1 Inhibitors include 7,8-dihydro-[1H or 2H]-imidazo[1,2-a]pyrazolo[4,3-e]pyrimidin-4(5H)-ones of Formula Ia:

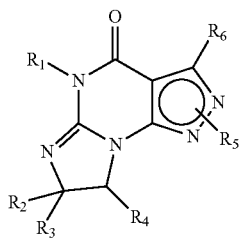

Formula Ia wherein
(i) $R_1$ is H or $C_{1-4}$ alkyl [e.g., methyl];
(ii) $R_4$ is H and $R_2$ and $R_3$ are, independently, H or $C_{1-4}$ alkyl [e.g., $R_2$ and $R_3$ are both methyl, or $R_2$ is H and $R_3$ is isopropyl], aryl, or arylalkyl;
or $R_2$ is H and $R_3$ and $R_4$ together form a di-, tri- or tetramethylene bridge [pref. wherein the $R_3$ and $R_4$ have the cis configuration, e.g., where the carbons carrying $R_3$ and $R_4$ have the R and S configurations respectively];
(iii) $R_5$ is attached to one of the nitrogens on the pyrazolo portion of formula Ia and is a substituted benzyl of formula B

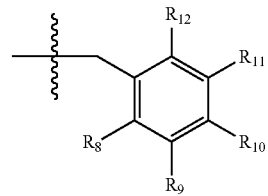

Formula B wherein $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), arylcarbonyl (e.g., benzoyl), alkyl sulfonyl or heteroarylcarbonyl; and (iv) $R_6$ is H, alkyl, aryl, heteroaryl, arylalkyl [e.g., benzyl], arylamino [e.g., phenylamino], heteroarylamino, arylalkylamino, N,N-dialkylamino, N,N-diarylamino, or N-aryl-N-(arylalkyl)amino [e.g. N-phenyl-N-(1,1'-biphen-4-ylmethyl)amino];

in free, salt or prodrug form.

The invention further provides the use of PDE 1 Inhibitors of Formula Ia as follows:

2.1: Formula Ia wherein $R_1$ is methyl;

2.2: Formula Ia or 2.1 wherein $R_4$ is H and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;

2.3: Formula Ia or 2.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;

2.4: Formula Ia, 2.1, 2.2 or 2.3 wherein $R_5$ is a moiety of formula B wherein $R_8$, $R_9$, $R_{11}$, and $R_{12}$ are H and $R_{10}$ is phenyl;

2.5: Formula Ia, 2.1, 2.2, or 2.3 wherein $R_5$ is a moiety of formula B wherein $R_8$, $R_9$, $R_{11}$, and $R_{12}$ are H and $R_{10}$ is pyridyl or thiadiazolyl;

2.6: Formula Ia, 2.1, 2.2, 2.3, 2.4, or 2.5 wherein $R_5$ is attached to the 2-position nitrogen on the pyrazolo ring;

2.7: Formula Ia, 2.1, 2.2, 2.3, 2.4, 2.5 or 2.6 wherein $R_6$ is benzyl;

2.8: Formula Ia, 2.1, 2.2, 2.3, 2.4, 2.5 or 2.6 wherein $R_6$ is phenylamino or phenylalkylamino (e.g., benzylamino); and/or 2.9: Formula Ia, 2.1, 2.2, 2.3, 2.4, 2.5, 2.6, 2.7, or 2.8 wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1;

in free or salt form.

In an another embodiment, the PDE 1 Inhibitors are compounds of Formula I wherein
(i) $R_1$ is methyl;
(ii) $R_2$, $R_3$ and $R_4$ are H;
(iii) n=1 and $R_a$ and $R_b$ are, independently, H or methyl;
(iv) $R_5$ is a moiety of Formula Q wherein $R_8$, $R_9$, $R_{11}$ and $R_{12}$ are H and $R_{10}$ is phenyl, pyridyl (for example pyrid-2-yl), or thiadiazolyl (e.g., 1,2,3-thiadiazol-4-yl);
(v) $R_6$ is benzyl, phenylamino or benzylamino;
in free or salt form.

In another embodiment, the PDE 1 Inhibitors are compounds of Formula I wherein (i) $R_1$ is methyl;
(ii) n=0;
(iii) $R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
(iv) $R_5$ is a substituted heteroarylmethyl, e.g., para-substituted with haloalkyl;

or $R_5$ is a moiety of Formula Q wherein $R_8$, $R_9$, $R_{11}$ and $R_{12}$ are H or halogen and $R_{10}$ is haloalkyl, phenyl, pyridyl (for example pyrid-2-yl), or thiadiazolyl (e.g., 1,2,3-thiadiazol-4-yl); and
(v) $R_6$ is benzyl, phenylamino or benzylamino;

in free or salt form.

In another embodiment, the PDE 1 Inhibitors are compounds of Formula Ia wherein (i) $R_1$ is methyl;
(ii) $R_2$ is H and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];
(iii) $R_5$ is a moiety of Formula B wherein $R_8$, $R_9$, $R_{11}$, and $R_{12}$ are H and $R_{10}$ is haloalkyl, phenyl, pyridyl (for example pyrid-2-yl), or thiadiazolyl (e.g., 1,2,3-thiadiazol-4-yl); and
(iv) $R_6$ is benzyl, phenylamino or benzylamino;

in free or salt form.

In another embodiment, the PDE 1 Inhibitors may be selected from the various formulae, as described in the subsequent paragraphs.

For example, PDE 1 Inhibitors include compounds according to Formulae II, III and IV.

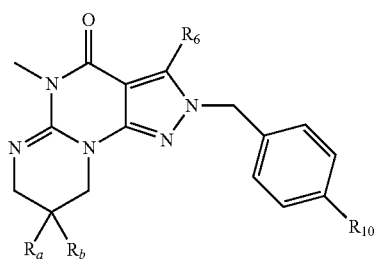

Formula II wherein $R_a$ and $R_b$ are, independently, H or $C_{1-4}$ alkyl;
$R_6$ is phenylamino or benzylamino;
$R_{10}$ is phenyl, pyridyl (for example pyrid-2-yl), or thiadiazolyl (e.g., 1,2,3-thiadiazol-4-yl);
in free or salt form.

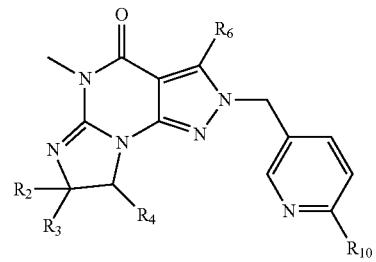

Formula III wherein $R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
$R_6$ is phenylamino or benzylamino;
$R_{10}$ is haloalkyl, phenyl, pyridyl (for example pyrid-2-yl), or thiadiazolyl (e.g., 1,2,3-thiadiazol-4-yl);
in free or salt form.

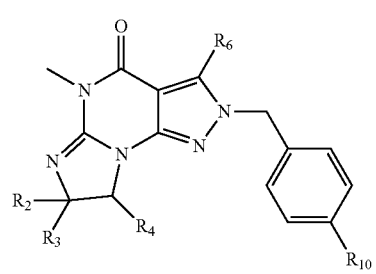

Formula IV wherein $R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_a$ is H; or $R_2$ and $R_3$ are H and $R_4$ is a $C_{1-4}$ alkyl;
$R_6$ is phenylamino or benzylamino;
$R_{10}$ is phenyl, pyridyl (for example pyrid-2-yl), or thiadiazolyl (e.g., 1,2,3-thiadiazol-4-yl);
in free or salt form.

In a preferred embodiment, the PDE 1 Inhibitors for use in the methods of treatment described herein are a 1,3,5-substituted 6,7-dihydro-1H-pyrazolo[4,3-d]pyrimidin-7-one, of formula V:

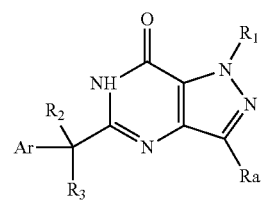

(V)

wherein
R$_a$ is methyl or C$_2$-C$_6$ alkyl;
R$_1$ is H or C$_1$-C$_4$ alkyl;
each of R$_2$ and R$_3$ is independently selected from H and C$_1$-C$_4$ alkyl, or R$_2$ is H or C$_1$-C$_4$ alkyl and R$_3$ is OH, C$_2$-C$_4$ alkanoyloxy or fluoro, or R$_2$ and R$_3$ when taken together represent C$_2$-C$_6$ alkylene, or R$_2$ and R$_3$ when taken together with the carbon atom to which they are attached represent a carbonyl group;
Ar is either (a)

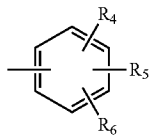

wherein
each of R$_4$, R$_5$ and R$_6$ is independently selected from
H
C$_1$-C$_4$ alkyl,
C$_1$-C$_4$ alkoxy,
C$_1$-C$_4$ alkoxy-Z—,
halo,
halo(C$_1$-C$_4$)alkyl,
phenoxy, optionally substituted by up to three substitutents each of which substitutent is independently selected from halo, C$_{1-4}$ alkyl, and C$_1$-C$_4$ alkoxy,
nitro,
hydroxy,
hydroxy-Z—,
C$_2$-C$_4$ alkanoyl,
amino,
amino-Z—,
(C$_1$-C$_4$ alkyl)NH,
(C$_1$-C$_4$ alkyl)$_2$N—,
(C$_1$-C$_4$ alkyl)NH—Z—,
(C$_1$-C$_4$ alkyl)$_2$N—Z—,
—COOH,
—Z—COOH,
—COO(C$_1$-C$_4$ alkyl),
—Z—COO(C$_1$-C$_4$ alkyl)
C$_1$-C$_4$ alkanesulphonamido,
C$_1$-C$_4$ alkanesulphonamido-Z—,
halo(C$_1$-C$_4$)alkanesulphonamido,
halo(C$_1$-C$_4$)alkanesulphonamido-Z—,
C$_1$-C$_4$ alkanamido,
C$_1$-C$_4$ alkanamido-Z—,
HOOC—Z—NH—,
HOOC—Z—NH—Z—,
(C$_1$-C$_4$ alkyl)OOC—Z—NH—,
(C$_1$-C$_4$ alkyl)OOC—Z—NH—Z—,
C$_1$-C$_4$ alkyl-NH—SO$_2$—NH—,
C$_1$-C$_4$ alkyl-NH—SO$_2$—NH—Z—,
(C$_1$-C$_4$ alkyl)$_2$-N—SO$_2$—NH—,
(C$_1$-C$_4$ alkyl)$_2$-N—SO$_2$—NH—Z—,
C$_1$-C$_4$ alkoxy CH=CH—Z—CONH—,
C$_1$-C$_4$ alkoxy CH=CHCONH
C$_1$-C$_4$ alkyl-SO$_2$—N(C$_1$-C$_4$ alkyl)-,
C$_1$-C$_4$ alkyl-SO$_2$—N(C$_1$-C$_4$ alkyl)-Z—,
(C$_1$-C$_4$ alkyl)NH—Z—SO$_2$—NH—,
(C$_1$-C$_4$ alkyl)$_2$N—Z—SO$_2$—NH—Z—,
(C$_1$-C$_4$ alkyl)NH—Z—SO$_2$—NH—Z—,
(C$_1$-C$_4$ alkyl)$_2$N—Z—SO$_2$—NH—Z—,
benzenesulphonamido, optionally ring substituted by up to three substitutents each of which is independently selected from halo, C$_{1-4}$ alkyl, and C$_1$-C$_4$ alkoxy,
C$_1$-C$_4$ alkanoyl-N(C$_1$-C$_4$ alkyl)-,
C$_1$-C$_4$ alkanoyl-N(C$_1$-C$_4$ alkyl)-Z—,
C$_1$-C$_4$ alkoxycarbonyl-CH(CH$_2$OH)NHSO$_2$—,
—SO$_3$H,
—SO$_2$NH$_2$,
H$_2$NOC—CH(CH$_2$OH)—NHSO$_2$—,
HOOC—Z—O—, and
(C$_1$-C$_4$ alkyl)OOC—Z—O—,
or optionally one of R$_4$, R$_5$ and R$_6$ is a G-Het group and wherein the others of R$_4$, R$_5$ and R$_6$ are independently selected from the R$_4$, R$_5$ and R$_6$ substitutents listed above;
Z is C$_1$-C$_4$ alkylene,
G is a direct link, Z, O, —SO$_2$NH—, SO$_2$, or —Z—N(C$_1$-C$_4$ alkyl)SO$_2$—,
Het is a 5- or 6-membered heterocyclic group containing 1, 2, 3 or 4 nitrogen heteroatoms; or 1 or 2 nitrogen heteroatoms and 1 sulphur heteroatom or 1 oxygen heteroatom; or the heterocyclic group is furanyl or thiophenyl; wherein the Het group is saturated or partially or fully unsaturated and optionally substituted by up to 3 substitutents, wherein each substitutent is independently selected from C$_1$-C$_4$ alkyl, oxo, hydroxy, halo, and halo(C$_1$-C$_4$)alkyl;
or (b) any one of the following bicyclic groups:
benzodioxolanyl,
benzodioxanyl,
benzimidazolyl,
quinolinyl,
indolyl,
quinazolinyl,
isoquinolinyl,
benzotriazolyl,
benzofuranyl,
benzothiophenyl,
quinoxalinyl, or
phthalizinyl,
wherein said bicyclic Ar groups are linked to the neighbouring —C(R$_2$R$_3$)— group via the benzo ring portion, and wherein the heterocyclic portion of said bicyclic Ar group is optionally partially or fully saturated, said group being optionally substituted by one or more of C$_1$-C$_4$ alkyl, halo, hydroxy, oxo, amino, and C$_1$-C$_4$ alkoxy;
or a pharmaceutically acceptable salt of the compound, or a pharmaceutically acceptable solvate of the compound or the salt.

For example, PDE 1 Inhibitors for use in the present invention include 1,3,5,-substituted, 6,7-dihydro-1H-pyrazolo[4,3-d]pyrimidin-7-one, in free or pharmaceutically acceptable salt form, particularly compounds of Formula V or the following formulae:
3.2 Of Formula V wherein R$_a$ is a C$_{2-5}$ alkyl group;
3.3 Of Formula V wherein R$_a$ is a C$_{2-4}$ alkyl group.
3.4 Of Formula V wherein R$_a$ is a C$_3$ alkyl group.
3.5 Of Formula V wherein R$_a$ is methyl
3.6 Of Formula V, 3.2, 3.3, 3.4 or 3.5 wherein R$_1$ is a C$_{1-6}$ alkyl group.
3.7 Of any of the preceding formulae wherein R$_1$ is a C$_{1-3}$ alkyl group.
3.8 Of any of the preceding formulae wherein R$_1$ is a methyl group.
3.9 Of any of the preceding formulae wherein R$_2$ is H.
3.10 Of any of the preceding formulae wherein R$_3$ is H.

3.11 Of any of the preceding formulae wherein $R_4$, $R_5$ and $R_6$ are independently selected from $H$, $(C_{1-4}$ alkyl$)_2$N—, $C_{1-4}$ alkanesulphonamido and benzenesulphonamido.

3.12 Of any of the preceding formulae wherein $R_4$, $R_5$ and $R_6$ are independently selected from H, diethylamino, methanesulphonamido and benzenesulphonamido.

3.13 Of any of the preceding formulae wherein Ar is 4-diethylaminophenyl.

3.14 Of any of the preceding formulae wherein Ar is 2-methanesulphonamidophenyl.

3.15 Of any of the preceding formulae wherein Ar is 4-benzenesulphonamidophenyl.

3.16 Of any of the preceding formulae wherein one of $R_4$, $R_5$ and $R_6$ is $(C_{1-4}$ alkyl$)_2$N— and wherein the other two of $R_4$, $R_5$ and $R_6$ are H.

3.17 Of any of the preceding formulae wherein one of $R_4$, $R_5$ and $R_6$ is diethylamino and wherein the other two of $R_4$, $R_5$ and $R_6$ are H.

3.18 Of any of the preceding formulae wherein $R_a$ is methyl.

3.19 Of any of the preceding formulae wherein $R_a$ is $C_2$-$C_6$ alkyl.

3.20 Of any of the preceding formulae wherein the compound is selected from the following:

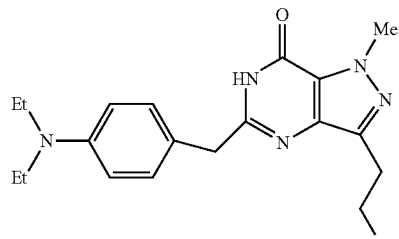

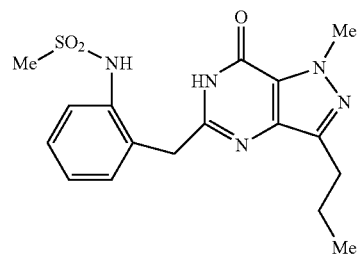

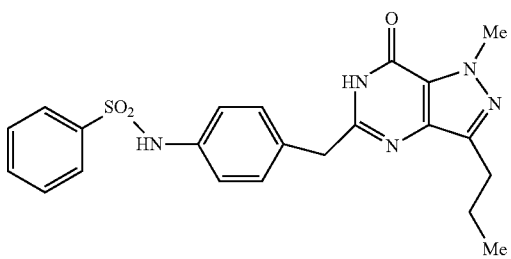

3.21 Of any of the preceding formulae wherein the compound is

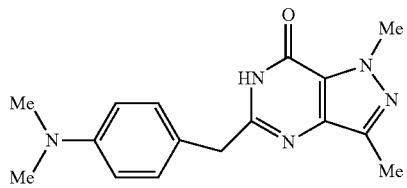 [SMILES: Cc1nn(C)c2c(=O)[nH]c(Cc3ccc(N(C)C)cc3)nc12]

3.22 A compound which is a 1,3,5,-substituted, 6,7-dihydro-1H-pyrazolo[4,3-d]pyrimidin-7-one, in free or pharmaceutically acceptable salt form, e.g. a compound of Formula V or according to any of formulae 3.2-3.21, wherein the compound inhibits phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1 below.

In another embodiment, the PDE 1 Inhibitors for use in the methods of treatment described herein are substituted imidazo[2,1-b]purin-4-one of Formula VIIa or VIIb:

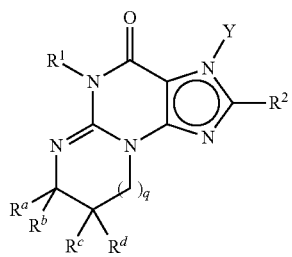

Formula VIIa

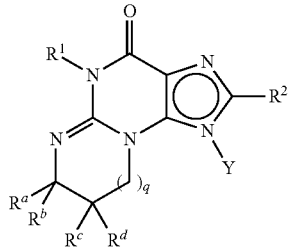

Formula VIIb in free, salt or prodrug form, including its enatiomers, diasterisomers and racemates, wherein:
i) q=0, 1 or 2;
ii) $R^1$, $R^a$, $R^b$, $R^c$ and $R^d$ are each independently H, alkyl, aryl, heteroaryl, cycloalkyl or heterocycloalkyl groups, wherein each alkyl group of $R^1$, $R^a$, $R^b$, $R^c$ and $R^d$ is independently unsubstituted or substituted with 1 to 5 independently selected $R^3$ moieties which can be the same or different, each $R^3$ moiety being independently selected from the group consisting of hydroxy, alkoxy, cycloalkoxy, aryloxy, alkylthio, arylthio, aryl, haloaryl, heteroaryl, cycloalkyl, heterocycloalkyl, amino, alkylamino, dialkylamino, cycloalkylamino and heterocycloalkylamino groups;
wherein each of the aryl, heteroaryl, cycloalkyl and heterocycloalkyl groups of $R^1$, $R^a$, $R^b$, $R^c$ and $R^d$ is independently unsubstituted or substituted with 1 to 5 independently selected $R^4$ moieties which can be the same or different, each $R^4$ moiety being independently selected from the group consisting of: halo, optionally substituted aryl (e.g., phenyl, chlorophenyl, methoxyphenyl), heteroaryl (e.g., pyridyl, pyrrolyl), nitro, cyano, haloalkyl, haloalkoxy, alkyl, alkoxy, cycloalkyl, heterocycloalkyl (e.g., pyrolidinyl, morpholin-4-yl, pyrrol-1-yl), cycloalkylalkyl, amino, alkylamino, dialkylamino, —$OCF_3$, acyloxy, —$OR^8$, —$C(O)R^9$, —$C(O)OR^8$, —$NR^{10}C(O)R^9$, —$NR^{10}C(O)OR^8$, —$NR^{10}S(O)_2R^9$, —$S(O)_{0-2}R^9$ groups, carbonyl when two hydrogens attached to the same carbon atom of the cycloalkyl or heterocycloalkyl group of R' are substituted, and =$CR^8R^9$ when two hydrogens attached to the same carbon atom of the cycloalkyl or heterocycloalkyl groups of $R^1$ are substituted, wherein each of the aryl, heteroaryl, cycloalkyl and heterocycloalkyl groups of the $R^3$ and $R^4$ moieties above is independently unsubstituted or substituted with 1 to 5 independently selected $R^{12}$ moieties which can be the same or different, each $R^{12}$ moiety being independently selected from the group consisting of: halo, phenyl, nitro, cyano, haloalkyl, haloalkoxy, alkyl, cycloalkyl, cycloalkylalkyl, amino, alkylamino, —$OCF_3$, acyloxy, —$OR^8$, —$C(O)R^9$, —$C(O)OR^8$, —$NR^{10}C(O)R^9$, —$NR^{10}C(O)OR^8$, —$NR^{10}S(O)_2R^9$, —$S(O)_{0-2}R^9$ groups, carbonyl when two hydrogens attached to the same carbon atom of the cycloalkyl or heterocycloalkyl group of $R^3$ or $R^4$ are substituted, and =$CR^8R^9$ when two hydrogens attached to the same carbon atom of the cycloalkyl or heterocycloalkyl group of $R^3$ or $R^4$ are substituted; or iii) $R^a$ and $R^b$, together with the carbon to which they are both attached, form a 4- to 7-membered cycloalkyl or heterocycloalkyl ring, and $R^c$ and $R^d$ are each independently H or an alkyl group; or iv) $R^a$ and $R^c$, together with the respective carbons to which they are attached, form a 4- to 7-membered cycloalkyl or heterocycloalkyl ring, and $R^b$ and $R^d$ are each independently H or an alkyl group, preferably $R^a$ and $R^c$ together have the cis configuration, e.g., where the carbons carrying $R^a$ and $R^c$ have the R and S configurations, respectively;

v) $R^2$ is H, halo, alkyl, haloalkyl, alkoxy, alkylthio, amino, aminosulfonyl, monoalkylamino, dialkylamino, hydroxyalkylamino, aminoalkylamino, carboxy, alkoxycarbonyl, aminocarbonyl or alkylaminocarbonyl group, wherein each alkyl group of $R^2$ is independently unsubstituted or substituted with 1 to 5 independently selected $R^{13}$ moieties which can be the same or different, each $R^{13}$ moiety being independently selected from the group consisting of halo, hydroxy, alkoxy, alkyl, aryl (e.g., phenyl, naphthyl) heteroaryl (e.g., 1H-imidazol-2-yl), cycloalkyl, heterocycloalkyl (e.g., pyrolidin-1-yl), amino, monoalkylamino or dialkylamino group, wherein each aryl group of $R^{13}$ is independently unsubstituted or substituted with 1 to 5 independently selected $R^4$ moieties which can be the same or different;

vi) Y is H or an alkyl group substituted with (i) an aryl, heteroaryl, cycloalkyl, hydroxy, alkoxy, amino, monoalkylamino or dialkylamino group, or (ii) an aryl group substituted with from one to three moieties each independently selected from the group consisting of: halo, alkyl, phenyl, hydroxy, alkoxy, phenoxy, amino, monoalkylamino and dialkylamino group;

vii) each $R^8$ is independently H, alkyl or aryl;

viii) each $R^9$ is independently H, alkyl, aryl or —$NR^{10}R^{11}$;

ix) each $R^{10}$ is independently H, alkyl, aryl, heteroaryl, arylalkyl or heteroarylalkyl, wherein each alkyl, aryl, heteroaryl, arylalkyl or heteroarylalkyl of $R^{10}$ is unsubstituted or independently substituted with 1 to 5 $R^{14}$ moieties which can be the same or different, each $R^{14}$ moiety being independently selected from the group consisting of: halo, alkyl, aryl, cycloalkyl, —$CF_3$, —$OCF_3$, —CN, —$OR^8$, —$CH_2OR^8$, —$C(O)OR^8$ and —$C(O)NR^8R^8$; and x) each $R^{11}$ is independently H, alkyl, aryl, heteroaryl, arylalkyl or heteroarylalkyl, wherein each alkyl, aryl, heteroaryl, arylalkyl or heteroarylalkyl of $R^{11}$ is unsubstituted or independently substituted with 1 to 5 $R^{14}$ moieties which can be the same or different.

The invention further provides the use of PDE 1 Inhibitors of Formula VIIa or VIIb, in free or salt form, as follows:

4.1: Formula VIIa or VIIb, wherein q=0, 1 or 2;

4.2: Formula VIIa or VIIb, wherein q=0;

4.3: Formula VIIa or VIIb or 4.1 or 4.2, wherein $R^1$ is alkyl;

4.4: Formula VIIa or VIIb or 4.1-4.2, wherein $R^1$ is methyl;

4.5: Formula VIIa or VIIb or 4.1-4.4, wherein $R^a$ and $R^c$, together with the respective carbons to which they are attached, form a 4- to 7-membered cycloalkyl or heterocycloalkyl ring, and $R^b$ and $R^d$ are each independently H or an alkyl group;

4.6: Formula VIIa or VIIb or 4.1-4.4, wherein $R^a$ and $R^c$, together with the respective carbons to which they are attached, form a 5-membered heterocycloalkyl ring, and $R^b$ and $R^d$ are each independently H;

4.7: Formula VIIa or VIIb or 4.1-4.4, wherein $R^a$ and $R^b$, together with the respective carbons to which they are attached, form a 5-membered heterocycloalkyl ring, and $R^c$ and $R^d$ are each independently H;

4.8: Formula VIIa or VIIb or 4.1-4.7, wherein $R^2$ is alkyl or haloalkyl;

4.9: Formula VIIa or VIIb or 4.1-4.7, wherein $R^2$ is biphenyl-4-ylmethyl;

4.10: Formula VIIa or VIIb or 4.1-4.7, wherein $R^2$ is benzyl;

4.11: Formula VIIa or VIIb or 4.1-4.7, wherein $R^2$ is cyclopentylmethyl;

4.12: Formula VIIa or VIIb or 4.1-4.7, wherein $R^2$ is cyclopropylmethyl;

4.13: Formula VIIa or VIIb or 4.1-4.12, wherein Y is benzyl; and/or 4.14: Of any of the preceding formulae wherein the compound is selected from the following:

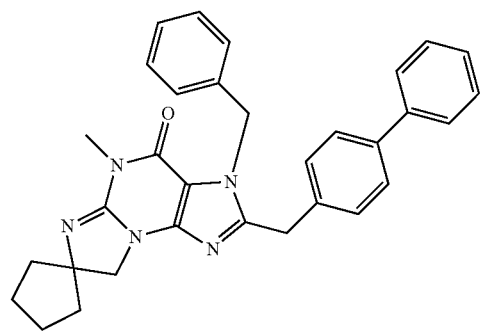

-continued

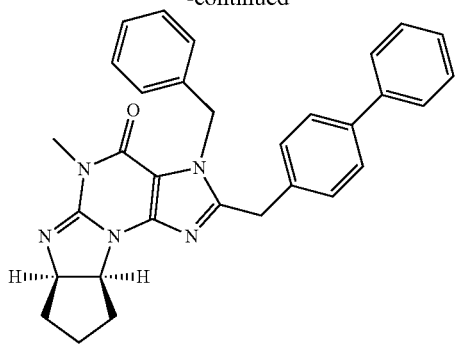

,

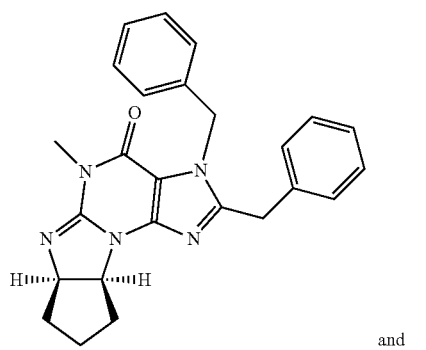

and

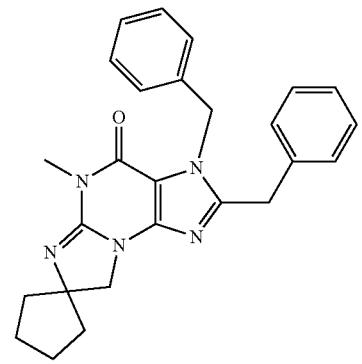

4.15: Of any of the preceding formulae wherein the compound is

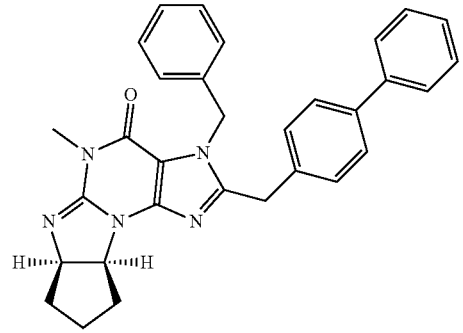 [SMILES: CN1C(=O)c2c(nc(Cc3ccc(-c4ccccc4)cc3)n2Cc2ccccc2)N2C1=N[C@@H]1CCC[C@@H]12]

4.16: A compound which is a substituted imidazo[2,1-b]purin-4-one, in free or pharmaceutically acceptable salt form, e.g. a compound of Formula VIIa or according to any of formulae 4.1-4.15, wherein the compound inhibits phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1 below.

Preferably, compounds of Formula VIIa or VIIb are selected from a group consisting of (6aR,9aS)-5,6a,7,8,9,9a-hexahydro-5-methyl-2,3-bis(phenylmethyl)-yclopent[4,5]imidazo[2,1-b]purin-4(3H)-one, (6aR,9aS)-2-(biphenyl-4-ylmethyl)-5,6a,7,8,9,9a-hexahydro-5-methyl-3-(phenylmethyl)cyclopent[4,5]imidazo[2,1-b]purin-4(3H)-one, 5'-methyl-2',3'-bis(phenylmethyl)spiro[cyclopentane-1,7'(8'H)-[3H]imidazo[2,1-b]purin]-4'(5'H)-one and 5'-methyl-2'-(biphenyl-3'-(phenylmethyl)spiro-[cyclopentane-1,7'(8'H)-[3H]imidazo[2,1-b]purin]-4(5'H)-one, in free or pharmaceutically acceptable salt form.

In an especially preferred embodiment, compound of Formula VIIa is (6aR,9aS)-2-(biphenyl-4-ylmethyl)-5,6a,7,8,9,9a-hexahydro-5-methyl-3-(phenylmethyl)cyclopent-[4,5]imidazo[2,1-b]purin-4(3H)-one, in free or salt form.

The numbering of substituted imidazo[2,1-b]purin-4-one of Formula VIIa or VIIb as described herein is shown below as an example, wherein q=0:

Formula VIIa

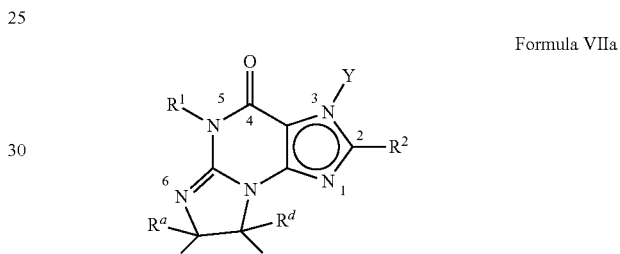

Formula VIIb

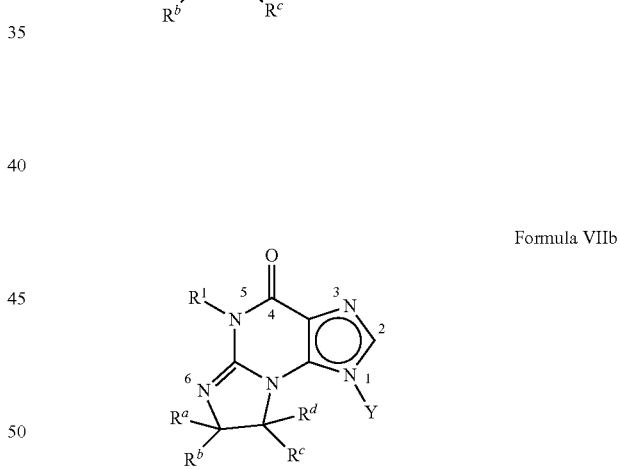

wherein q=1:

Formula VIIa

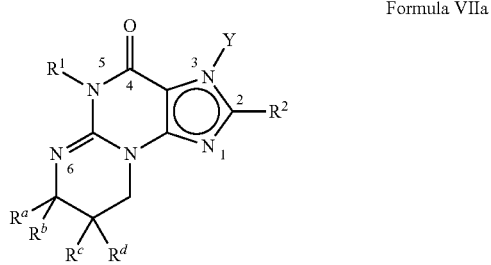

-continued

Formula VIIb

In another embodiment, the PDE 1 Inhibitors for use in the methods of treatment described herein are Compounds of Formula VIIIa or VIIIb:

Formula VIIIa

Formula VIIIb in free or salt form, wherein:
J is oxygen or sulfur,
$R^1$ is hydrogen, alkyl or alkyl substituted with aryl or hydroxy;
$R^2$ is hydrogen, aryl, heteroaryl, cycloalkyl, alkyl or alkyl substituted with aryl, heteroaryl, hydroxy, alkoxy, amino, monoalkyl amino or dialkylamino, or —$(CH_2)_m$ $TCOR^{20}$ wherein m is an integer from 1 to 6, T is oxygen or —NH— and $R^{20}$ is hydrogen, aryl, heteroaryl, alkyl or alkyl substituted with aryl or heteroaryl;
$R^3$ is hydrogen, halo, trifluoromethyl, alkoxy, alkylthio, alkyl, cycloalkyl, aryl, aminosulfonyl, amino, monoalkylamino, dialkylamino, hydroxyalkylamino, aminoalkylamino, carboxy, alkoxycarbonyl or aminocarbonyl or alkyl substituted with aryl, hydroxy, alkoxy, amino, monoalkylamino or dialkylamino;
$R^a$, $R^b$, $R^c$ and $R^d$ independently represent hydrogen, alkyl, cycloalkyl or aryl; or ($R^a$ and $R^b$) or ($R^c$ and $R^d$) or ($R^b$ and $R^c$) can complete a saturated ring of 5- to 7-carbon atoms, or ($R^a$ and $R^b$) taken together and ($R^b$ and $R^c$) taken together, each complete a saturated ring of 5- to 7-carbon atoms, wherein each ring optionally can contain a sulfur or oxygen atom and whose carbon atoms may be optionally substituted with one or more or the following: alkenyl, alkynyl, hydroxy, carboxy, alkoxycarbonyl, alkyl or alkyl substituted with hydroxy, carboxy or alkoxycarbonyl; or such saturated ring can have two adjacent carbon atoms which are shared with an adjoining aryl ring; and
n is zero or one.

The invention further provides the use of PDE 1 Inhibitors of Formula VIIIa or VIIIb, in free or salt form, as follows:
5.1: Formula VIIIa or VIIIb, wherein J=O.
5.2: Formula VIIIa or VIIIb or 5.1, wherein $R^1$ is alkyl.
5.3: Formula VIIIa or VIIIb, 5.1 or 5.2, wherein $R^2$ is hydrogen, benzyl, 4-chlorobenzyl, cyclohexylmethyl or trimethylacetoxymethyl.
5.4: Formula VIIIa or VIIIb, 5.1, 5.2 or 5.3, wherein $R^3$ is hydrogen, or alkyl such as methyl or ethyl.
5.5: Formula VIIIa or VIIIb, 5.1, 5.2, 5.3 or 5.4, wherein n is zero; and
5.6: Formula VIIIa or VIIIb, 5.1, 5.2, 5.3, 5.4 or 5.5, wherein $R^a$ and $R^b$ form a saturated 5 membered ring, or ($R^b$ and $R^c$) form a saturated 5, 6 or 7 membered ring, or ($R^a$ and $R^b$) and ($R^b$ and $R^c$) each complete a saturated ring and each ring contains 5 or 6 carbon atoms.

The invention further provides the use of PDE 1 Inhibitors of Formula VIIIa or VIIIb, in free or salt form, selected from the following:
cis-5,6a,7,8,9,9a-Hexahydro-5-methyl-3-(phenylmethyl) cyclopenta[4,5]imidazo-[2,1-b]purin-4-one;
7,8-Dihydro-5-methyl-3-(phenylmethyl)-3H-imidazo[2,1-b]purin-4(5H)-one;
cis-6a,7,8,9,10,10a-Hexahydro-5-methyl-3-(phenylmethyl)-3H-benzimidazo[2,1-b]purin-4(5H)-one;
5,7,8,9-Tetrahydro-5-methyl-3-(phenylmethyl)pyrimido[2,1-b]purin-4(3H)-one;
7,8-Dihydro-8-phenyl-5-methyl-3-(phenylmethyl)-3H-imidazo[2,1-b]purin-4(5H)-one;
5',7'-Dihydro-5'-methyl-3'-(phenylmethyl)spiro[cyclohexane-1,8'-(8H)imidazo-[2,1-b]purin]4'(3'H)-one;
cis-5,6a,11,11a-Tetrahydro-5-methyl-3-(phenylmethyl) indeno[1',2':4,5]imidazo-[2,1-b]purin-4(3H)-one;
5',7'-Dihydro-2',5'dimethyl-3'-(phenylmethyl) spiro{cyclohexane-1,7'(8'H)-imidazo[2,1-b]purin}-4'-(3'H)-one;
7,8-Dihydro-2,5,7,7,8(R,S)-pentamethyl-3H-imidazo[2,1-b]purin-4(5H)-one;
cis-5,6a,7,11b-Tetrahydro-5-methyl-3-(phenylmethyl)indeno[2',1',:4,5]imidazo[2,1-b]purin-4(3H)-one;
cis-5,6a,7,8,9,9a-Hexahydro-2,5-dimethyl-3-(phenylmethyl)cyclopent[4,5]-imidazo[2,1-b]purin-4-(3H)-one;
5'-Methyl-3'-(phenylmethyl)-spiro[cyclopentane-1,7'-(8'H)-(3'H)imidazo[2,1-b]purin]-4-(5'H)-one;
7,8-Dihydro-2,5,7,7-tetramethyl-3-(phenylmethyl)-3H-imidazo[2,1-b]purin-4(5'H)-one;
7,8-Dihydro-7(R)-phenyl-2,5-dimethyl-3-(phenylmethyl)-3H-imidazo[2,1-b]purin-4(5H)-one;
7,8-Dihydro-2,5-dimethyl-3,7(R)-bis(phenylmethyl)-3H-imidazo[2,1-b]purin-4(5H)-one;
(±)-7,8-Dihydro-2,5-dimethyl-7-ethyl-3-(phenylmethyl)-3H-imidazo[2,1-b]purin-4(5H)-one;
6a(S)-7,8,9,10,10a(R)-Hexhydro-2,5-dimethyl-3-(phenylmethyl)-3H-benzimidazo[2,1-b]purin-4(5H)-one;
6a(R)-7,8,9,10,10a(S)-hexahydro-2,5-dimethyl-3-(phenylmethyl)-3H-benzimidazo-[2,1-b]purin-4(5H)-one;
7,8-Dihydro-2,5-dimethyl-7(R)-isopropyl-3-(phenylmethyl)-3H-imidazo[2,1-b]purin-4(5H)-one;
7,8-Dihydro-2,5,7(R)-trimethyl-3-(phenylmethyl)-3H-imidazo[2,1-b]purin-4(5H)-one;

cis-7,7a,8,9,10,10a-Hexahydro-2,5-dimethyl-3-(phenylmethyl)-3H-cyclopenta-[5,6]pyrimido[2,1-b]purin-4(5H)-one;

7,8-Dihydro-2,5-dimethyl-7(S)-(1-methylpropyl)-3-(phenylmethyl)-3H-imidazo-[2,1-b]purin-4(5H)-one;

7,8-Dihydro-2,5-dimethyl-7(R)-(2-methylpropyl)-3-(phenylmethyl)-3H-imidazo-[2,1-b]purin-4(5H)-one;

7,8-Dihydro-2,5-dimethyl-7(R,S)-(methoxycarbonyl)-3-(phenylmethyl)-3H-imidazo[2,1-b]purin-4(5H)-one;

7,8-Dihydro-2,5-dimethyl-7(R,S)-(1-propyl)-3-(phenylmethyl)-3H-imidazo[2,1-b]purin-4(5H)-one;

7,8-Dihydro-2,5-dimethyl-7(S)-(1-methylethyl)-3-(phenylmethyl)-3H-imidazo[2,1-b]purin-4(5H)-one;

7,8-Dihydro-2,5,7,7,8(R,S)-pentamethyl-3H-imidazo[2,1-b]purin-4(5H)-one;

5,7,8,9-Tetrahydro-2,5,7,9(R,S)-pentamethyl-3-(phenylmethyl)-pyrimido[2,1-b]purin-4(3H)-one;

5,6a(R),7,8,9,9a(S)-Hexahydro-2,5-dimethyl-3-(phenylmethyl)cyclopent-[4,5]imidazo[2,1-b]purin-4(3H)-one;

5,6a(S),7,8,9,9a(R)-Hexahydro-2,5-dimethyl-3-(phenylmethyl)cyclopent-[4,5]imidazo[2,1-b]purin-4(3H)-one;

cis-6a,7,8,9,10,10a-Hexahydro-2,5-dimethyl-3-(phenylmethyl)-3H-benzimidazo[2,1-b]purin-4(5H)-one;

5',7'-Dihydro-2',5'-dimethyl-3'-(phenylmethyl)spiro[cyclohexane-1,8-(8H)-imidazo[2,1-b]purin]-4-(3'H)-one;

cis-5,6a,7,8,9,9a-Hexahydro-2,5-dimethyl-3-(phenylmethyl)cyclohept-[6,7]imidazo[2,1-b]purin-4(3H)-one;

cis-5,6a,7,8,9,9a-Hexahydro-5-methyl-2-ethyl-3-(phenylmethyl)cyclopent-[4,5]imidazo[2,1-b]purin-4(3H)-one;

cis-6a,7,8,9,10,10a-Hexahydro-5-methyl-2-ethyl-3-(phenylmethyl)-3H-benzimidazo[2,1-b]purin-4-(5H)-one;

cis-5,6a,7,8,9,9a-Hexahydro-5-methyl-2-ethyl-3-(phenylmethyl)cyclopent-[4,5]imidazo[2,1-b]purin-4(3H)-one;

cis-5,6a,7,8,9,9a-Hexahydro-5-methyl-2-phenyl-3-(phenylmethyl)cyclopent-[4,5]imidazo[2,1-b]purin-4(3H)-one;

cis-6a,7,8,9,10,10a-Hexahydro-5-methyl-2-phenyl-3-(phenylmethyl)-3H-benzimidazo[2,1-b]purin-4(5H)-one;

cis-5,6a,7,8,9,9a-Hexahydro-5-methylcyclopenta[4,5]imidazo[2,1-b]purin-4(3H)-one;

cis-5,6a,7,8,9,9a-Hexahydro-2,5-dimethylcyclopenta[4,5]imidazo[2,1-b]purin-4(3H)-one;

cis-5,6a(R), 7,8,9,9a(S)-Hexahydro-2,5-di-methylcyclopent[4,5]imidazo[2,1-b]purin-4(3H)-one;

2',5'-dimethyl-spiro{cyclopentane-1,7'-(8'H)-(3'H)-imidazo[2,1-b]purin}-4'(5'H)-one;

7,8-Dihydro-2,5-dimethyl-7(R)-(1-methylethyl)-3H-imidazo[2,1-b]purin-4(5H)-one;

7,8-Dihydro-2,5,7,7-tetramethyl-3H-imidazo[2,1-b]purin-4(5H)-one;

7,8-Dihydro-2,5-dimethyl-7(S)-(1-methylethyl)-3H-imidazo[2,1-b]purin-4(5H)-one;

6a(R),7,8,9,10,10a(S)-Hexahydro-2,5-dimethyl-3H-benzimidazo[2,1-b]purin-4(5H)-one;

5',7'-Dihydro-2',5'-dimethylspiro{cyclohexane-1,7-(8'H)-imidazo[2,1-b]purin}-4'(3'H)-one;

cis-5,6a,7,8,9,9a-Hexahydro-5-methyl-3-(phenylmethyl)cyclopenta[4,5]-imidazo[2,1-b]purin-4(3H)-thione;

5,6a(R),7,8,9,9a(S)-Hexahydro-2,5-dimethyl-3-(phenylmethyl)cyclopent-[4,5]imidazo[2,1-b]purin-4(3H)-thione;

cis-5,6a,7,8,9,9a-Hexahydro-5-methyl-3-(4-chlorophenylmethyl)cyclopenta[4,5]-imidazo[2,1-b]purin-4(3H)-one;

cis-5,6a,7,8,9,9a-Hexahydro-5-methyl-3-(cyclohexylmethyl)cyclopent[4,5]-imidazo[2,1-b]purin-4(3H)-one;

cis-5,6a,7,8,9,9a-Hexahydro-5-methyl-3-(2-naphthylmethyl)cyclopent[4,5]-imidazo[2,1-b]purin-4(3H)-one;

5,6a(R),7,8,9,9a(S)-Hexahydro-2,5-dimethyl-3-(4-bromophenylmethyl)-cyclopent[4,5]imidazo[2,1-b]purin-4(3H)-one;

5,6a(R)-7,8,9,9a(S)-Hexahydro-2,5-dimethyl-3-(4-methoxyphenylmethyl)-cyclopent[4,5]imidazo[2,1-b]purin-4(3H)-one;

cis-5,6a,7,8,9,9a-Hexahydro-2,3,5-trimethylcyclopent[4,5]imidazo[2,1-b]purin-4(3H)-one;

cis-5,6a,7,8,9,9a-Hexahydro-2-(hydroxymethyl)-5-methyl-3-(phenylmethyl)-cyclopent[4,5]imidazo[2,1-b]purin-4(3H)-one;

cis-5,6a,7,8,9,9a-Hexahydro-2-methylthio-5-methyl-3-(Phenylmethyl)cyclopent-[4,5]imidazo[2,1-b]purin-4(3H)-one;

cis-3,4,5,6a,7,8,9,9a-Octahydro-5-methyl-4-oxo-3-(phenylmethyl)cyclopent-[4,5]imidazo[2,1-b]purin-2-carboxylic acid;

cis-3,4,5,6a,7,8,9,9a-Octahydro-5-methyl-4-oxo-3-(phenylmethyl)cyclopent-[4,5]imidazo[2,1-b]purin-2-carboxylic acid, methyl ester;

cis-5,6a,7,8,9,9a-Hexahydro-2-bromo-5-methyl-3-(phenylmethyl)cyclopent[4,5]imidazo[2,1-b]purin-4(3H) one;

cis-5,6a,7,8,9,9a-Hexahydro-2-(methylaminosulfonyl)-5-methyl-3-(phenylmethyl)cyclopent[4,5]imidazo[2,1-b]purin-4(3H)one;

cis-1-Cyclopentyl-5,6a,7,8,9,9a-hexahydro-5-methylcyclopent[4,5]imidazo[2,1-b]purin-4-(1H)one;

cis-5,6a,7,8,9,9a-Hexahydro-3,5-bis-(phenylmethyl)cyclopent(4,5)imidazo(2,1-b)purin-4(3H)one;

cis-6a,7,8,9,10,10a-Hexahydro-3,5-bis-(phenylmethyl)-3H-benzimidazo[2,1-b]purin-4(5H)one;

cis-3-Cyclopentyl-5,6a,7,8,9,9a-hexahydro-5-methylcyclopent[4,5]imidazo(2,1-b)purin-4(3H)one;

5'-Methyl-3'-(phenylmethyl)spiro[cyclopentane-1,7-(8'H)-(3'H)imidazo[2,1-b]purin]-4-(5'H)one;

2',5'-Dimethyl-3'-(phenylmethyl)-spiro[cyclopentane-1,7-(8'H)-(3'H)imidazo[2,1-b]purin]-4-(5'H)one;

cis-5,6a,(R)7,8,9,9a(S)-Hexahydro-5-methyl-3-(phenylmethyl)cyclopent[4,5]-imidazo(2,1-b)purin-4(3H)one;

cis-3-Cyclopentyl-5,6a,7,8,9,9a-Hexahydro-2,5-dimethylcyclopent[4,5]imidazo-[2,1-b]purin-4(3H)one;

5'-Methyl-2'-trifluoromethyl-3'-(phenylmethyl)spiro{cyclo-pentane-1,7'(8'H)-(3'H)imidazo[2,1-b]purin}-4-(5'H)-one;

7,8-Dihydro-5,7,7-trimethyl-2-trifluoromethyl-3-(phenylmethyl)-3H-imidazo[2,1-b]purin-4(5H)-one;

(+/−)-cis-5,6a,7,8,9,9a-Hexahydro-5-methyl-2-trifluoromethyl-3-(phenylmethyl)-cyclopent[4,5]imidazo[2,1-b]purin-4(3H)-one;

(+/−)-6a,7,8,9,9a,10,11,11 a-Octahydro-2,5-dimethyl-3-(phenylmethyl)-3H-pentaleno[6a',1':4,5]imidazo[2,1-b]purin-4(5H)-one;

(+)-6a,7,8,9,9a,10,11,11a-Octahydro-2,5-dimethyl-3-phenylmethyl-3H-pentaleno[6a',1':4,5]imidazo[2,1-b]purin-4(5H)-one;

(−)-6a,7,8,9,9a,10,11,11a-Octahydro-2,5-dimethyl-3-phenylmethyl-3H-pentaleno[6a',1':4,5]Imidazo[2,1-b]purin-4(5H)-one;

(+/−) 6a,7,8,9,9a,10,11,11a-Octahydro-2,5-dimethyl-3H-pentaleno[6a',1':4,5]-imidazo[2,1-b]purin-4(5H)-one;

(+)-6a,7,8,9,9a,10,11,11a-Octahydro-2,5-dimethyl-3H-pentaleno[6a',1':4,5]-imidazo[2,1-b]purin-4(5H)-one;

(−)-6a,7,8,9,9a,10,11,11a-Octahydro-2,5-dimethyl-3H-pentaleno[6a',1':4,5]-imidazo[2,1-b]purin-4(5H)-one;

6a,7,8,9,10,10a,11,12,13,13a-Decahydro-2,5-dimethyl-(3-phenylmethyl)-napth[1,8a-d]imidazo[2,1-b]purin-4(5H)one;

7(R)-Cyclohexyl-7,8-dihydro-2,5-dimethyl-3-(phenylmethyl)-3H-imidazo[2,1-b]purin-4(3H)-one;

7(R)-Cyclohexyl-7,8-dihydro-2,5-dimethyl-3H-imidazo[2,1-b]purin-4(5H)-one;

7(S)-Cyclohexyl-7,8-dihydro-2,5-dimethyl-3-(phenylmethyl)-3H-imidazo[2,1-b]purin-4(3H)-one;

7(S)-Cyclohexyl-7,8-dihydro-2,5-dimethyl-3H-imidazo[2,1-b]purin-4(5H)-one;

5,6a(R),7,8,9,9a(S)-Hexahydro-2,5-dimethyl-[3-(trimethylacetoxy)methyl]-cyclopent[4,5]imidazo[2,1-b]purin-4(3H)-one;

5,6a(R),7,8,9,9a(S)-Hexahydro-2,5-dimethyl-3-(4-pyridylmethyl)cyclopent-[4,5]imidazo[2,1-b]purin-4(3H)-one;

5,6a(R),7,8,9,9a(S)-Hexahydro-2,5-dimethyl-3-[2-(4-morpholinyl)-ethyl]cyclopent[4,5]imidazo[2,1-b]purin-4(3H)-one;

5,6a(R),7,8,9,9a(S)-Hexahydro-2,5-dimethyl-3-[acetoxymethyl]cyclopent-[4,5]imidazo[2.1-b]purin-4(3H)-one;

5,6a,7,8,9,9a-Hexahydro-2,5,6a-trimethyl-3-(phenylmethyl)cyclopent-[4,5]imidazo[2,1-b]purin-4(3H)-one;

5,6a(R),7,8,9,9a(S)-Hexahydro-2,5,6a-trimethyl-3-(phenylmethyl)-cyclopent[4,5]imidazo[2,1-b]purin-4(3H)-one;

5,6a(S),7,8,9,9a(R)-Hexahydro-2,5,6a-trimethyl-3-(phenylmethyl)-cyclopent[4,5]imidazo[2,1-b]purin-4(3H)-one;

cis-6a,7,8,9,10,10a-Hexahydro-2,5,7-trimethyl-3-(phenylmethyl)-3H-benzimidazo[2,1-b]purin-4(5H)-one;

cis-5,6a,7,8,9,9a-Hexahydro-2,5,6a-trimethylcyclopent[4,5]imidazo[2,1-b]purin-4(3H)-one; or cis-[6a,7,8,9,10,10a-Hexahydro-2,5,7-trimethyl-3H-benzimidazo[2,1-b]purin-4(5H)-one].

In another embodiment, the PDE 1 Inhibitors for use in the methods of treatment described herein are Compounds of Formula IXa or IXb:

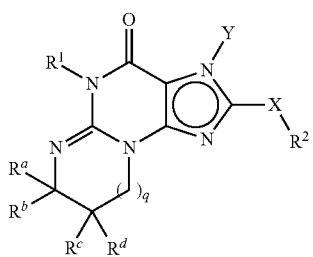

Formula IXa

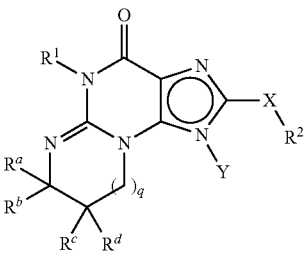

Formula IXb or a pharmaceutically acceptable salt thereof, wherein, q=0 or 1;

$R^1$ is H, cycloalkyl, alkyl, $R^{23}$-alkyl- or $R^{26}$;

$R^a$, $R^b$ and $R^c$ are, independently of one another, each H, alkyl, cyoloalkyl, aryl, $R^{22}$-aryl- or $R^{24}$-alkyl-; or $R^a$ and $R^b$, together with the carbon to which they are both attached, form a 4- to 7-membered ring, and $R^c$ is H or alkyl; or $R^a$ and $R^c$, together with the respective carbons to which they are attached, form a 4- to 7-membered ring, and $R^b$ is H or alkyl;

(i) X is a bond;
 Y is aryl-alkyl or $R^{22}$-aryl-alkyl-; and
 $R^2$ is monohaloalkyl, polyhaloalkyl, provided that it is not trifluoromethyl, azido, cyano, oximino, cycloalkenyl, heteroaryl, $R^{22}$-heteroaryl- or $R^{27}$-alkyl-;

(ii) X is a bond;
 Y is aryl-alkyl or $R^{22}$-aryl-alkyl-; and
 $R^2$ is H, halo, —CONHR$^6$, —CONR$^6$R$^7$, —CO$_2$R$^6$, monohaloalkyl, polyhaloalkyl, azido, cyano, —C=N—OR$^6$, cycloalkyl, cycloalkylalkyl, $R^{26}$, aminosulfonyl, alkyl or $R^{23}$-alkyl- (iii) X is —O— or —S—;
 Y is aryl-alkyl or $R^{22}$-aryl-alkyl-; and
 $R^2$ is $R^{26}$, cycloalkyl cycloalkylalkyl, heterocycloalkyl, cycloalkenyl or $R^{26}$-alkyl-;

(iv) X is —O— or —S—;
 Y is aryl-alkyl or $R^{22}$-aryl-alkyl-; and
 $R^2$ is alkyl, $R^{26}$, cycloalkyl, cycloalkylalkyl, heterocycloalkyl, cycloalkenyl or $R^{28}$-alkyl-;

(v) X is —SO— or —SO$_2$—;
 Y is aryl-alkyl or $R^{22}$-aryl-alkyl-; and
 $R^2$ is alkyl, $R^{26}$, cycloalkyl, cycloalkylalkyl, heterocycloalkyl, cycloalkenyl or $R^{28}$-alkyl-;

(vi) X is —NR$^8$—;
 Y is aryl-alkyl or $R^{22}$-aryl-alkyl-; and
 $R^2$ is $(R^{29})_p$-alkyl-, cycloalkyl, $(R^{30})_p$-cycloalkyl-, cycloalkenyl, $(R^{39})_p$—cycloalkenyl-, heterocycloalkyl or $(R^{30})_p$-heterocycloalkyl-:

(vii) X is —NR$^8$—;
 Y is aryl-alkyl or $R^{22}$-aryl-alkyl-; and
 $R^2$ is alkyl, $R^{26}$, cycloalkyl, cycloalkylalkyl, heterocycloalkyl, cycloalkenyl or $R^{31}$-alkyl-; or (viii) X is —C≡C—;
 Y is aryl-alkyl or $R^{22}$-aryl-alkyl-; and
 $R^2$ is alkyl, $R^{26}$, cycloalkyl, cycloalkylalkyl or $R^{23}$-alkyl-;

where, $R^6$ is H or $R^7$;

$R^7$ is alkyl, cycloalkyl or cycloalkylalkyl;

$R^8$ is heterocycloalkyl or $R^6$;

$R^{21}$ is 1-6 substituents each independently selected from the group consisting of halo, hydroxy, alkoxy, phenoxy, phenyl, nitro, aminosulfonyl, cyano, monohaloalkyl, polyhaloalkyl, thiol, alkylthio, cyoloalkyl, cycloalkyl-alkyl, amino, alkylamino, acylamino, carboxyl, —C(O)OR$^{34}$, carboxamido, —OCF$_3$ and acyloxy;

$R^{22}$ is 1-6 substituents each independently selected from the group consisting of alkyl and $R^{21}$;

$R^{23}$ is cycloalkoxy aryloxy, alkylthio, arylthio, cycloalkyl or $R^{28}$;

$R^{24}$ is cycloalkyl or $R^{26}$;

$R^{25}$ is hydroxy, alkoxy, amino, monoalkylamino, dialkylamino or $R^{26}$;

$R^{26}$ is aryl, $R^{22}$-aryl-, heteroaryl or $R^{22}$-heteroaryl-;

$R^{27}$ is cycloalkoxy, aryloxy, alkylthio, arylthio, heteroaryl, $R^{22}$-heteroaryl-, cycloalkyl, heterocycloalkyl, cycloalkenyl, cycloalkylamino or heterocycloalkylamino;

$R^{28}$ is cycloalkylamino, heterocycloalkylamino or $R^{25}$;

$R^{29}$ is alkoxy, cycloalkylamino, heterocycloalkylamino or $R^{26}$;

$R^{30}$ is halo, hydroxy, alkoxy, amino, aminosulfonyl, cyano, monohaloalkyl, polyhaloalkyl, thiol, alkylthio, alkyl, cyoloalkyl, cycloalkylalkyl or acyloxy;

$R^{31}$ is cycloalkyl or $R^{28}$;

$R^{34}$ is alkyl, aryl, aralkyl and heteroaryl; and p is 1 to 4.

6.1 The invention further provides the use of PDE 1 Inhibitors of Formula IXa or IXb, in free or salt form, selected from the following:

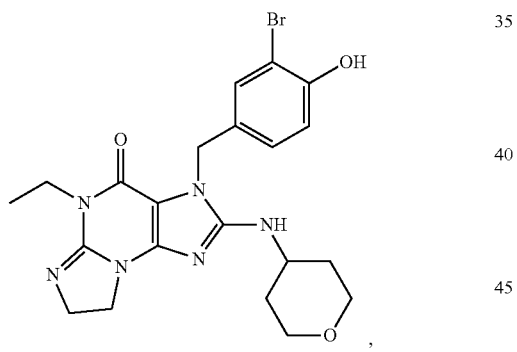

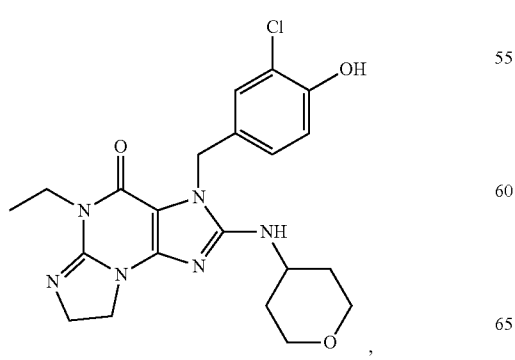

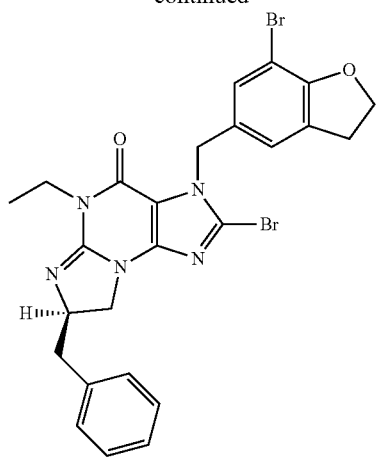

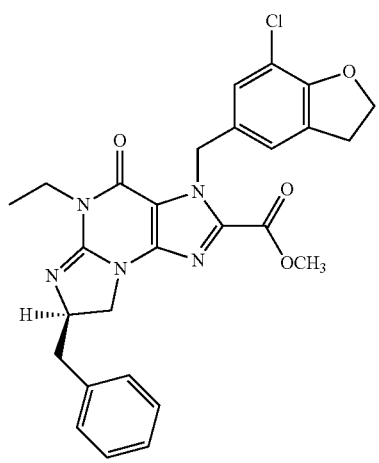

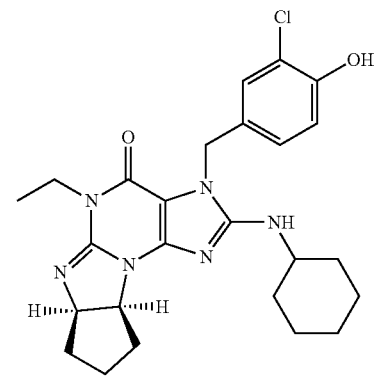

27
-continued
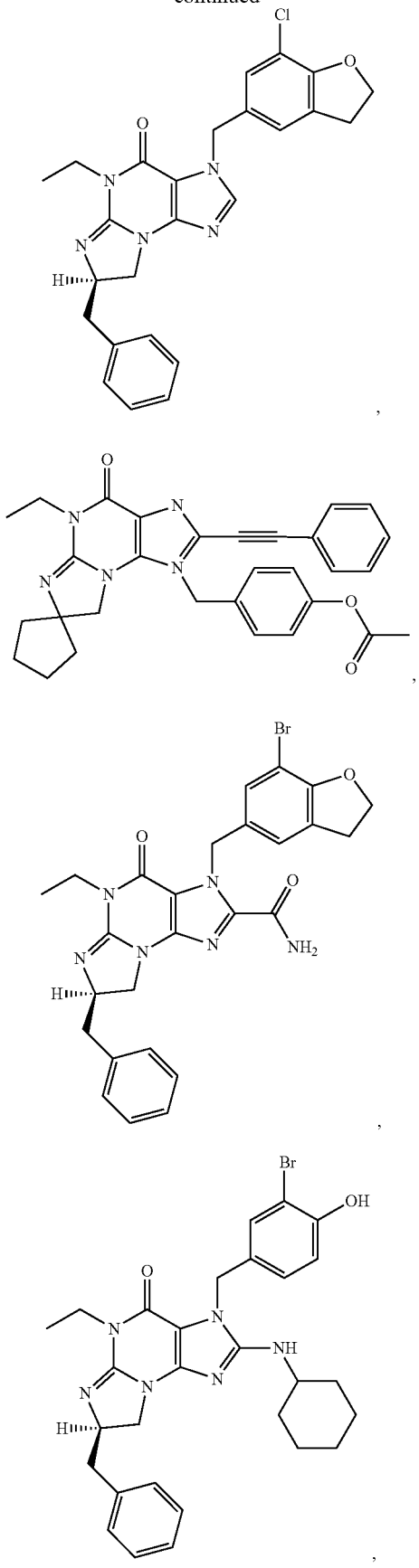
28
-continued
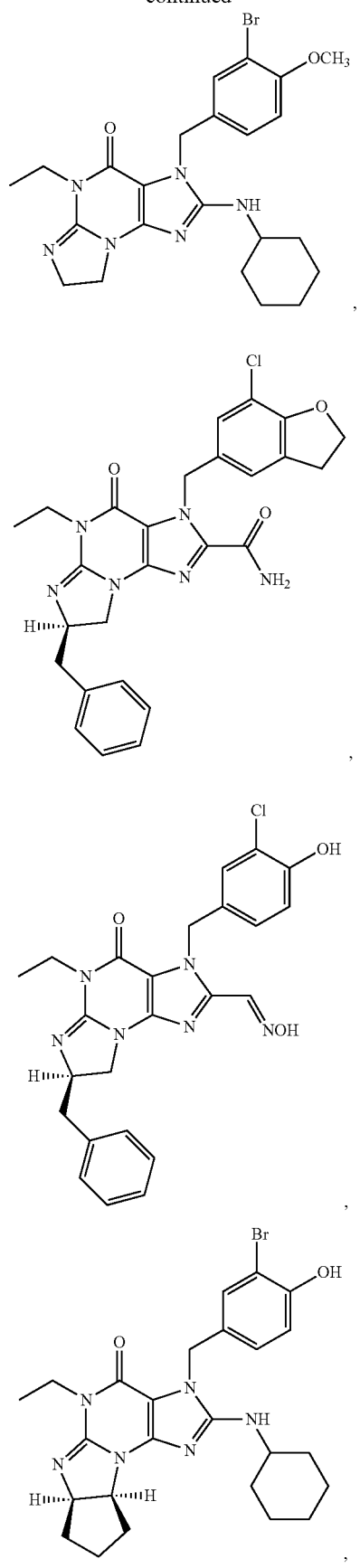

29
-continued
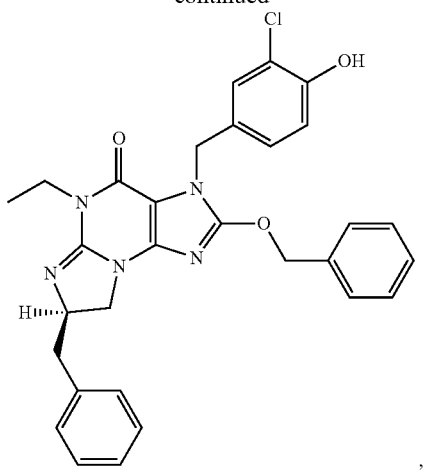
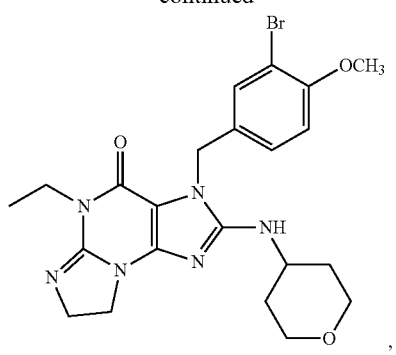
30
-continued
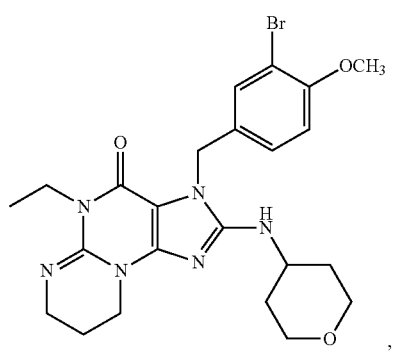
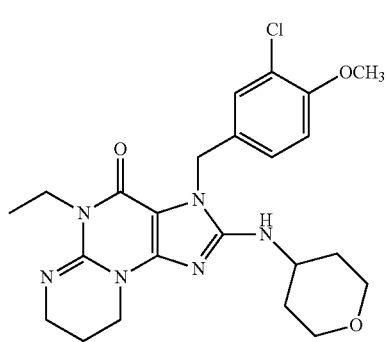
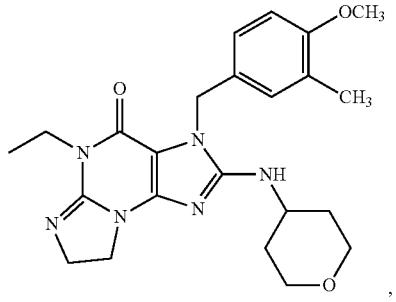
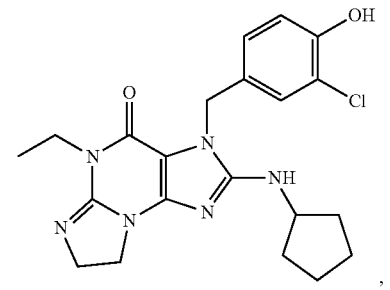

31
-continued
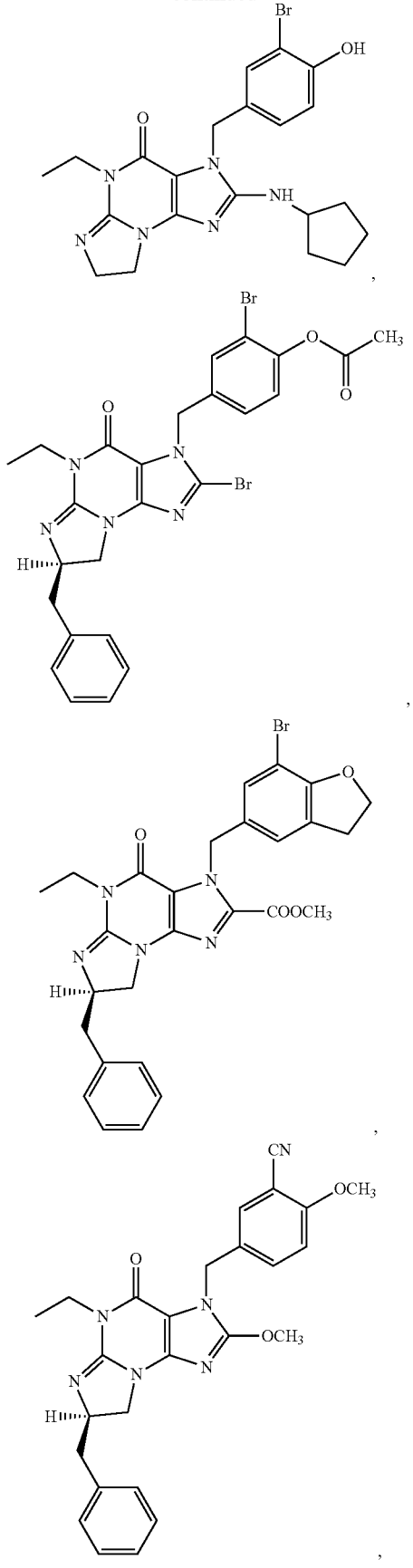
32
-continued
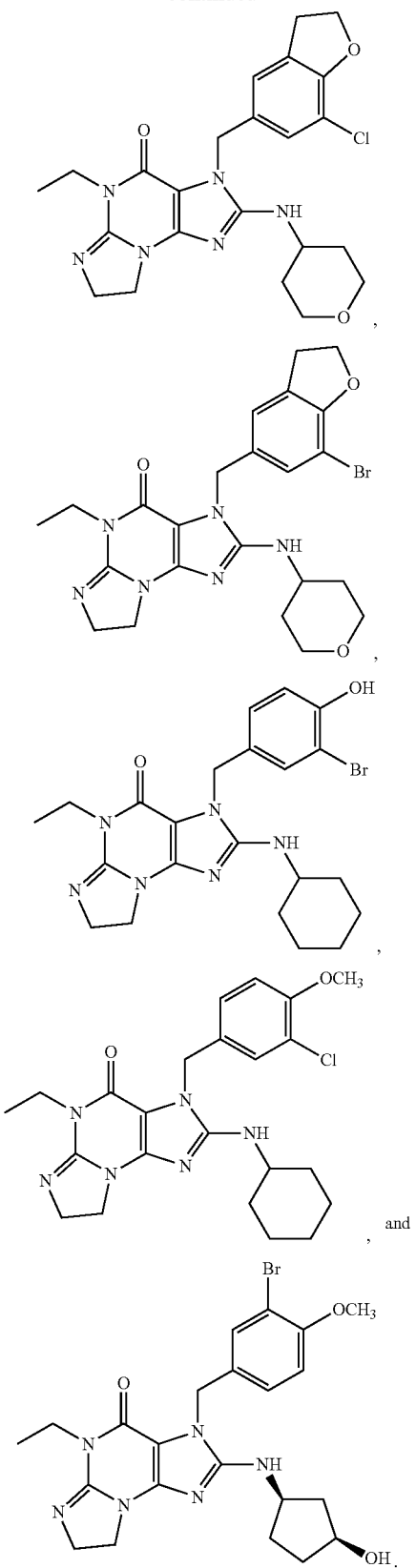
In another embodiment, the invention provides the use of PDE 1 Inhibitors of Formula X:

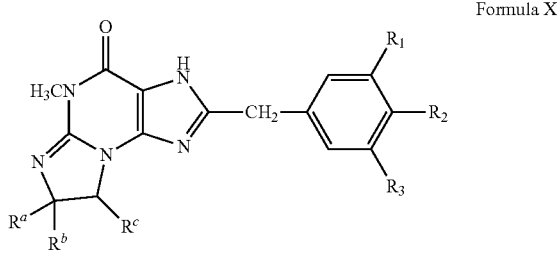

Formula X in free or a pharmaceutically acceptable salt thereof, wherein:

$R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring; and $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons.

In a further embodiment, the invention provides the use of PDE 1 Inhibitors of Formula X as follows:

7.1 Formula X, wherein $R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring;

7.2 Formula X or 7.1, wherein $R_1$ is H, methoxy or trifluoromethyl;

7.3 Formula X or 7.1 or 7.2, wherein $R_1$ is H;

7.4 Formula X or any of 7.1-7.3, wherein $R_2$ is selected from a group consisting of H, halo (e.g., F, Cl), methoxy, methyl, trifluoromethyl, dimethylamino, phenyl, methoxyphenyl-, —$OCF_3$, 3,4-$OCH_2O$—, pyrolidin-1-yl, pyrol-1-yl and morpholin-4-yl;

7.5 Formula X or any of 7.1-7.4, wherein $R_1$ and $R_2$ together with the carbon atoms to which they are attached forma a benzene ring;

7.6 Formula X or any of 7.1-7.5, wherein $R_3$ is H or methoxy;

7.7 Formula X or any of 7.1-7.6, wherein $R_3$ is H;

7.8 Formula X or any of 7.1-7.7, wherein $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons;

7.9 Formula X or any of 7.1-7.8, wherein $R^a$ is hydrogen and $R^b$ and $R^c$ together with the carbon atoms to which they are attached, form a saturated ring of 5 carbons, and wherein $R_1$, $R_2$ and $R_3$ are as defined in the following table

| $R_1$ | $R_2$ | $R_3$ |
|---|---|---|
| H | H | H |
| —$OCH_3$ | H | H |
| H | F | H |
| H | —$OCH_3$ | H |
| H | OH | H |
| H | —$CH_3$ | H |
| H | $(CH_3)_2N$— | H |
| —$OCH_3$ | —$OCH_3$ | —$OCH_3$ |
| —$OCH_3$ | —$OCH_3$ | H |
| —$CF_3$ | H | H |
| H | $C_2H_5$— | H |
| H | —$OCF_3$ | H |
| H | —N(pyrrolidinyl) | H |
| H | —N(pyrrolyl) | H |
| H | 3,4-$OCH_2O$— | H |
| H | —N(morpholinyl) | H |
| H | —C$_6$H$_4$—$OCH_3$ | H |
| $R_1$ and $R_2$, together with the carbon atoms to which they are attached form a benzene ring | | H |
| H | Cl | H |

7.10 Formula X or any of 7.1-7.9, selected from a group consisting of

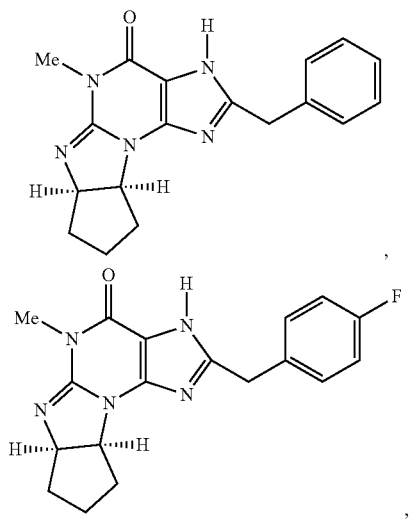

,

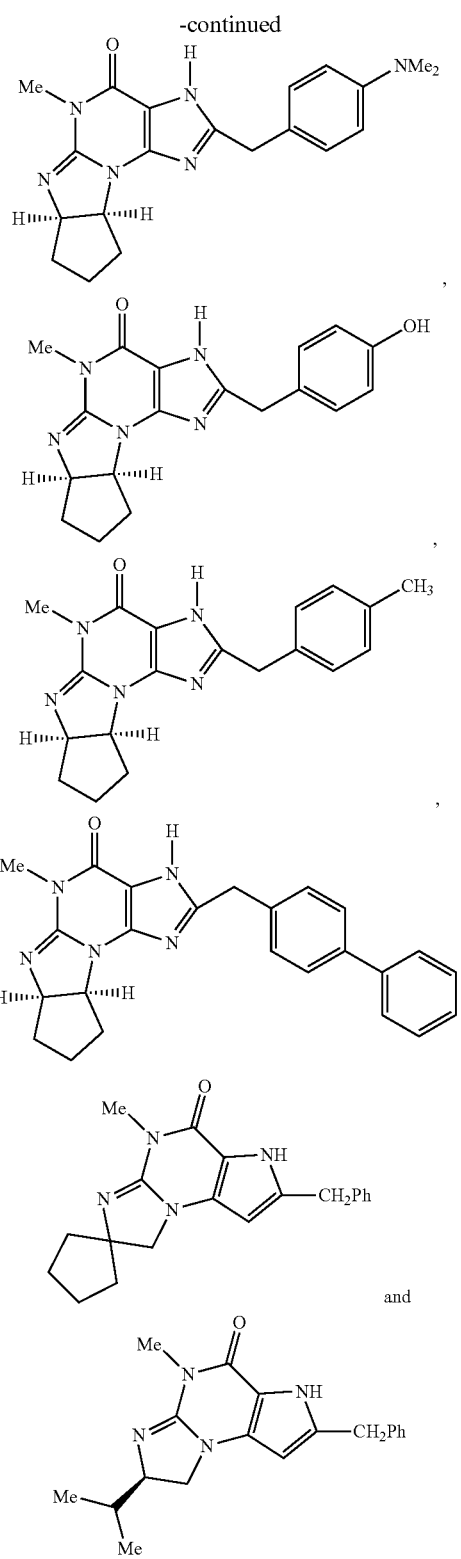

7.11 Formula X or any of 7.1-7.9, selected from a group consisting of:

2'-benzyl-5'-methyl-spiro[cyclopentane-1',7'(8'H)-[3'H]-imidazo[2,1-b]purin]-4'-(5'H)-one;

2'-benzyl-5,7,7-trimethyl-3H-imidazo[2,1-b]purin-4-(5H)-one;

(+)-2-benzyl-7,8-dihydro-5-methyl-7-(1-methylethyl)-1H-imidazo[2,1-b]-purin-4(5H)-one;

(+,−)-6a,7,8,9,9a,10,11,11a-octahydro-5-methyl-2-(3,4-methylene-dioxyphenylmethyl)-3H-pentalen[6a,1:4,5]imidazo[2,1-b]purin-4(5H)-one; and (+)-cis-6a,7,9,9a-tetrahydro-5-methyl-2-[4-(trifluoromethyl)-phenylmethyl]-3H-furo[3',4':4,5]imidazo[2,1-b]purin-4(5H)-one, in free or salt form.

7.12 Formulae X or 7.1-7.11, wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1;

In another embodiment, the invention provides the use of PDE 1 Inhibitors selected from the following:

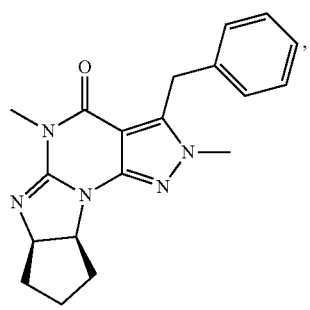

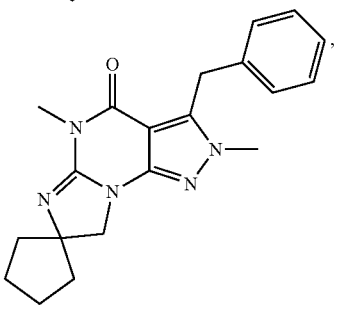

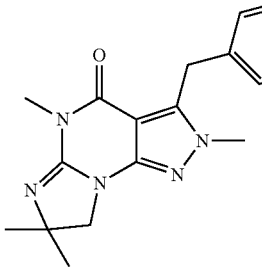

and

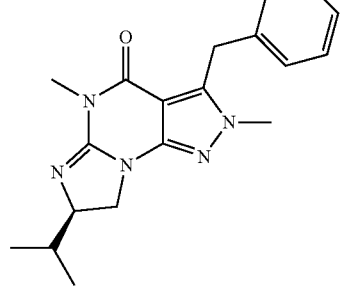

in free or salt form (Formula XI).

The invention also provides novel 2-(optionally hetero)arylmethyl-3-(optionally hetero)arylamino-[2H]-pyrazolo[3,4-d]pyrimidine-4,6(5H,7H)-diones, in free, salt or prodrug form (hereinafter "Compounds of the Invention"). The (optionally)hetero aryl moiety at the 2-position is preferably benzyl or pyridyl methyl para-substituted relative to the point of attachment with aryl or heteroaryl, e.g., substituted with phenyl, pyridyl or thiadiazolyl. These compounds are surprisingly found to selectively inhibit phosphodiesterase 1 (PDE1) activity, e.g., PDE1A, PDE1B, and PDE1C activity, especially PDE1B activity.

Preferably, the Compounds of the Invention are pyrazolo[3,4-d]pyrimidine-4,6(5H,7H)-diones of formula XII

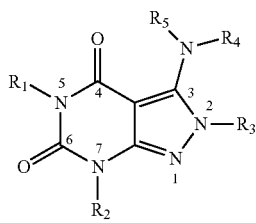

Formula XII
wherein
(i) $R_1$ is H or alkyl (e.g., methyl);
(ii) $R_2$ is H, alkyl (e.g., isobutyl, 2-methylbutyl, 2,2-dimethyl propyl), cycloalkyl (e.g., cyclopentyl, cyclohexyl), haloalkyl (e.g., trifluoromethyl, 2,2,2-trifluoroethyl), alkylaminoalkyl (e.g., 2-(dimethylamino)ethyl), hydroxyalkyl (e.g., 3-hydroxy-2-methyl propyl), arylalkyl (e.g., benzyl), heteroarylalkyl (e.g., pyridylmethyl), or alkoxyarylalkyl (e.g., 4-methoxybenzyl);
(iii) $R_3$ is a substituted heteroarylaklyl, e.g., substituted with haloalkyl
or
$R_3$ is attached to one of the nitrogens on the pyrazolo portion of Formula XII and is
a moiety of Formula C

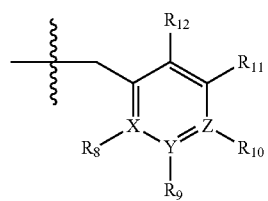

Formula C wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;

(iv) $R_4$ is aryl (e.g., phenyl) or heteroaryl; and
(v) $R_5$ is H, alkyl, cycloalkyl (e.g., cyclopentyl), heteroaryl, aryl, p-benzylaryl (e.g., biphenyl-4-ylmethyl);
wherein "alk" or "alkyl" refers to $C_{1-6}$ alkyl and "cycloalkyl" refers to $C_{3-6}$ cycloalkyl; in free, salt or prodrug form The invention further provides compounds of Formula XII as follows:
8.1 Formula XII wherein $R_1$ is methyl;
8.2 Formula XII or 12.1 wherein $R_2$ is $C_{1-6}$ alkyl;
8.3 Formula 12.2 wherein $R_2$ is isobutyl, 2,2-dimethyl propyl, or 2-methylbutyl;
8.4 Formula XII or 12.1 wherein $R_2$ is hydroxy $C_{1-6}$ alkyl;
8.5 Formula XII or 12.1 wherein $R_2$ is 3-hydroxy-2-methyl propyl;
8.6 Formula XII or 12.1 wherein $R_2$ is $C_{1-6}$ alkoxy-benzyl;
8.7 Formula 12.6 wherein $R_2$ is p-methoxybenzyl;
8.8 Formula XII or 12.1 wherein $R_2$ is $C_{3-6}$ cycloalkyl;
8.9 Formula 12.8 wherein $R_2$ is cyclopentyl or cyclohexyl;
8.10 Formula XII or 12.1 wherein $R_2$ is $C_{1-6}$ haloalkyl;
8.11 Formula 12.10 wherein $R_2$ is 2,2,2-trifluoroethyl;
8.12 Any of the preceding formulae wherein $R_3$ is a moiety of Formula A wherein $R_8$, $R_9$, $R_{11}$ and $R_{12}$ are each H and $R_{10}$ is phenyl;
8.13 Any of the preceding formulae XII-12.11 wherein $R_3$ is a moiety of Formula A wherein $R_8$, $R_9$, $R_{11}$ and $R_{12}$ are each H and $R_{10}$ is pyridyl or thiadiazolyl;
8.14 Formula 12.13 wherein $R_3$ is a moiety of Formula A wherein $R_8$, $R_9$, $R_{11}$ and $R_{12}$ are each H and $R_{10}$ is 2-pyridyl;
8.15 Any of the preceding formulae wherein $R_4$ is phenyl;
8.16 Any of the preceding formulae wherein $R_5$ is H;
8.17 Any of the preceding formulae wherein X, Y and Z are all C;
8.18 Any of the preceding formulae wherein $R_2$ is tetrahydrofuran-2-ylmethyl;
8.19 Any of the preceding formulae wherein $R_{10}$ is pyrimidinyl;
8.20 A compound of formula 12.19 wherein the pyrimidinyl is 5-fluoropyrmidinyl;
8.21 Any of the preceding formulae wherein $R_{10}$ is pyrazol-1-yl;
8.22 Any of the preceding formulae wherein $R_{10}$ is 1,2,4-triazol-1-yl;
8.23 Any of the preceding formulae wherein $R_{10}$ is aminocarbonyl;
8.24 Any of the preceding formulae wherein $R_{10}$ is methylsulfonyl;
8.25 Any of the preceding formulae wherein $R_{10}$ is 5-methyl-1,2,4-oxadiazol-3-yl;
8.26 Any of the preceding formulae wherein $R_{10}$ is 5-fluoropyrimidin-2-yl;
8.26 Any of the preceding formulae wherein $R_4$ is 4-fluorophenyl;
8.27 Any of the preceding formulae wherein $R_{10}$ is trifluoromethyl;
8.28 Any of the preceding formulae wherein $R_3$ is a moiety of Formula C, X and Z are C, and Y is N;
8.29 A compound selected from the compounds of Examples 1-24 below; and/or
8.30 Any one of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example I; such compounds according to any of the preceding formulae being in free, salt or prodrug form.

In an especially preferred embodiment, the Compounds of the Invention are compounds of Formula XII wherein
(i) $R_1$ is methyl;
(ii) $R_2$ is $C_{1-6}$ alkyl;
(iii) $R_3$ is a moiety of Formula C wherein X, Y and Z are all C and $R_8$, $R_9$, $R_{11}$ and $R_{12}$ are each H and $R_{10}$ is phenyl, pyridyl (for example, pyrid-2-yl), or thiadiazolyl (e.g., 1,2,3-thiadiazol-4-yl);
(iv) $R_4$ is phenyl; and
(v) $R_5$ is H; in free or salt form.

For example, the methods of treatment include compounds according to Formula XIII:

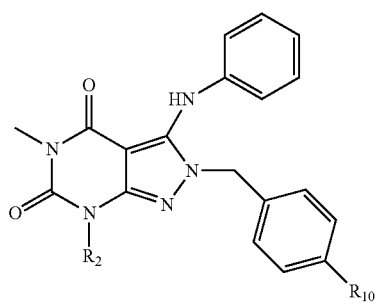

Formula XIII wherein $R_2$ is H, alkyl (e.g., isobutyl, 2-methylbutyl, 2,2-dimethyl propyl), cycloalkyl (e.g., cyclopentyl, cyclohexyl), heteroaryl (e.g., pyridyl), aryl (e.g., phenyl), haloalkyl (e.g., trifluoromethyl, 2,2,2-trifluoroethyl), alkylaminoalkyl (e.g., 2-(dimethylamino)ethyl), hydroxyalkyl (e.g., 3-hydroxy-2-methyl propyl), arylalkyl (e.g., benzyl), or alkoxyarylalkyl (e.g., 4-methoxybenzyl);
wherein "alk" or "alkyl" refers to $C_{1-6}$ alkyl; and
$R_{10}$ is phenyl, pyridyl (for example, pyrid-2-yl) or thiadiazolyl (for example,
1,2,3-thiadiazol-4-yl);
in free, salt or prodrug form In certain embodiments, the Compounds of the Invention are compounds of Formula XIII wherein
$R_2$ is H, alkyl (e.g., isobutyl, 2-methylbutyl, 2,2-dimethyl propyl), cycloalkyl (e.g., cyclopentyl, cyclohexyl, tetrahydrofuran-2-ylmethyl), heteroaryl (e.g., pyridyl), aryl (e.g., phenyl), haloalkyl (e.g., trifluoromethyl, 2,2,2-trifluoroethyl), alkylaminoalkyl (e.g., 2-(dimethylamino)ethyl), hydroxyalkyl (e.g., 3-hydroxy-2-methyl propyl), arylalkyl (e.g., benzyl), or alkoxyarylalkyl (e.g., 4-methoxybenzyl);
and $R_{10}$ is phenyl, pyridyl (for example, pyrid-2-yl), pyrimidinyl (e.g., 5-fluoropyrimidin-2-yl), pyrazolyl (e.g. pyrazol-1-yl), thiadiazolyl (for example, 1,2,3-thiadiazol-4-yl), haloalkyl (e.g., trifluoromethyl), alkylsulfonyl (e.g., methylsulfonyl), oxadiazolyl (e.g., 5-methyl-1,2,4-oxadiazol-3-yl), aminocarbonyl (e.g., so as to form a 4-benzamide structure), triazolyl (e.g., 1,2,4-triazol-1-yl);
wherein "alk" or "alkyl" refers to $Ci_{-6}$ alkyl;
in free, salt or prodrug form.

If not otherwise specified or clear from context, the following terms as used herein have the following meetings:
a. "Alkyl" as used herein is a saturated or unsaturated hydrocarbon moiety, preferably saturated, preferably one to seven carbon atoms in length, which may be linear or branched, and may be optionally substituted, e.g., mono-, di-, or tri-substituted, e.g., with halogen (e.g., chloro or fluoro), hydroxy, or carboxy.
b. "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy.
c. "Heterocycloalkyl" as used herein is a saturated or unsaturated nonaromatic hydrocarbon moiety, preferably saturated, preferably comprising three to nine carbon atoms, at least one atom selected from a group consisting of N, O or S, at least some of which form a nonaromatic mono- or bicyclic, or bridged cyclic structure, and which may be optionally substituted, e.g., with halogen (e.g., chloro or fluoro), hydroxy, or carboxy. Examples of heterocycloalkyl include pyrrolidinyl (e.g., pyrrolidin-1-yl), morpholinyl (e.g., morpholin-4-yl),
d. "Aryl" as used herein is a mono or bicyclic aromatic hydrocarbon (e.g., phenyl, naphthyl), preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).
e. "Heteroaryl" as used herein is an aromatic moiety wherein one or more of the atoms making up the aromatic ring is sulfur or nitrogen rather than carbon, e.g., pyridyl, thiadiazolyl, pyrrolyl (e.g., pyrrol-2-yl) or imidazolyl (e.g., 1H-imidazol-2-yl), which may be optionally substituted, e.g., with alkyl, halogen, haloalkyl, hydroxy or carboxy.

PDE 1 Inhibitors may exist in free or salt form, e.g., as acid addition salts. In this specification unless otherwise indicated language such as PDE 1 Inhibitors is to be understood as embracing the compounds in any form, for example free or acid addition salt form, or where the compounds contain acidic substituents, in base addition salt form. The PDE 1 Inhibitors are intended for use as pharmaceuticals, therefore pharmaceutically acceptable salts are preferred. Salts which are unsuitable for pharmaceutical uses may be useful, for example, for the isolation or purification of free PDE 1 Inhibitors or their pharmaceutically acceptable salts.

PDE 1 Inhibitors may in some cases also exist in prodrug form, for example when the compounds contain physiologically hydrolysable and acceptable esters. As used herein, "physiologically hydrolysable and acceptable ester" means esters of PDE 1 Inhibitors which are hydrolysable under physiological conditions to yield acids (in the case of PDE 1 Inhibitors which have hydroxy substituents) or alcohols (in the case of PDE 1 Inhibitors which have carboxy substituents) which are themselves physiologically tolerable at doses to be administered. As will be appreciated the term thus embraces conventional pharmaceutical prodrug forms.

The pharmaceutical composition, which includes a PDE 1 inhibitor and optionally, an intraocular pressure lowering agent, may be formulated according to known methods for preparing pharmaceutically useful compositions. The pharmaceutically acceptable carrier can include diluents, adjuvants, and vehicles, as well as implant carriers, and inert, non-toxic solid or liquid fillers, diluents, or encapsulating material that does not react with the active ingredients used in the compositions. Examples include, but are not limited to, phosphate buffered saline, physiological saline, water, and emulsions, such as oil/water emulsions.

The pharmaceutical carrier can be a solvent or dispersing medium containing, for example, ethanol, polyol (for example, glycerol, propylene glycol, liquid polyethylene glycol, and the like), suitable mixtures thereof, and vegetable oils. Formulations containing pharmaceutically acceptable carriers are described in a number of sources which are well known and readily available to those skilled in the art. For example, Remington's The Science and Practice of Pharmacy, 21$^{st}$ edition, describes formulations that can be used in connection with the compositions.

Methods of making and formulating the PDE 1 Inhibitors, novel intermediates useful for making PDE 1 Inhibitors, and methods of using the PDE 1 Inhibitors for treatment of diseases are generally disclosed in EP 0201188 (or U.S. Pat. No. 4,666,908) and EP 0911333 (or U.S. Pat. No. 6,235,742); PCT/US2006/022066; PCT/US2006/033179; WO 03/042216 (U.S. Pat. No. 6,943,171); U.S. Pat. Nos. 6,969,719; 5,939,419; EP 0 538 332 (U.S. Pat. No. 5,393,755); Xia et al., J. Med. Chem. (1997), 40, 4372-4377 and Ahn et al., J. Med. Chem. (1997), 40, 2196-2210, the contents of each of which are incorporated herein by reference by their entirety.

In another example, an ophthalmic composition which includes ophthalmic solutions, may be prepared using at least one of the PDE-1 inhibitors or a combination. Procedures for preparing ophthalmic compostions are described in Remington's: The Science and Practice of Pharmacy, 21$^{st}$ ed., see pgs. 856-863, for example.

In one example, the effective amount of the PDE 1 inhibitor in the ophthalmic solution is a subthreshold amount.

The ophthalmic composition can additionally include an agent known to lower intraocular pressure, preferably a subthreshold effective amount of the additional agent.

The agent may be an adrenergic agonist, a beta-adrenergic antagonist, a prostaglandin or prostaglandin analog or a muscarinic analog, or an agent that raises cyclic nucleotides, a prostanoid, bimatoprost, brimonidine tartrate, or brimonidine tartrate/timolol maleate, or a combination. In addition agnonists selective for a particular receptor subtype may be used, such as alpha-2 adrenergic receptor agonist, for example. Other agents known to treat glaucoma may be used.

The ophthalmic composition may be prepared in the form of a gel-forming solution, a semi-solid aqueous gel or other ophthalmic gels, an ophthalmic suspension ophthalmic ointment or an ophthalmic emulsion, or an ophthalmic solution, Other forms of ophthalmic delivery include a viscoelastic solution such as a solution containing a highly purified fraction of sodium hyaluronate, chrondroitin sulfate, or purified hydroxypropyl methylcellulose, for example.

Other examples of preparing ophthalmic compositions known to a person of ordinary skill in the art may be utilized.

However, other means of drug administrations are well within the scope of the composition. Systemic therapeutic means may also be utilized.

The PDE-1 inhibitors disclosed in this application may be combined with a subthreshold effective amount of glaucoma drugs by Allergan.

In one example, a subthreshold effective amount of a PDE-1 inhibitor and a subthreshold amount of bimatoprost ophthalmic solution, marketed as LUMIGAN® is administered to a patient in need thereof, for treatment or management of glaucoma.

In one example, a subthreshold effective amount of a PDE-1 inhibitor and a subthreshold amount of brimonidine tartrate ophthalmic solution, marketed as ALPHAGAN® is administered to a patient in need thereof, for treatment or management of glaucoma.

In one example, a subthreshold effective amount of a PDE-1 inhibitor and a subthreshold amount of briimonidine tartrate/timolol ophthalmic solution, marketed as COMBIGAN® is administered to a patient in need thereof, for treatment or management of glaucoma.

In another example, a subthreshold effective amount of a PDE-1 inhibitor and a subthreshold amount of a combination of LUMIGAN®, ALPHAGAN®, and COMBIGAN®, may be administered together.

In another example, an effective amount of an ophthalmic prostaglandin, or a prostaglandin analog or a combination of the prostaglandin and the prostaglandin analog may be combined with an effective amount of the PDE-1 inhibitor to treat glaucoma, elevated intraocular pressure, or symptoms of glaucoma. The effective amount is interpreted to include a subthreshold amount. In one example, a subthreshold amount of a prostaglandin or a prostaglandin analog or a combination may be combined with a subthreshold amount of a PDE-1 inhibitor, to treat glaucoma, or elevated intraocular pressure. Examples of prostaglandins and prostaglandin analogs include travoprost, latanoprost, bimatroprost, an active ingredient in LUMIGAN,® unoprostone, and unoprostone isopropyl, an active ingredient in RESCULA.® There have been reports in the literature that many of the prostaglandins and their analogs such as bimatroprost and latanoprost have been associated with side effects that include increased eyelash growth and browning of the iris. Other side effects also include eye redness and itchy eyes. Thus, a subthreshold amount of a prostaglandin or an analog or a combination may be combined with an effective dosage of the PDE-1 inhibitor, to reduce or treat glaucoma, or elevated intraocular pressure, without the associated side effects.

In another embodiment, the disclosed PDE 1 inhibitors, either alone, or in combination with other therapeutic agents, may be used for the treatment of diabetic retinopathy, a disease caused by complications of diabetes mellitus. Conventional treatments include laser surgery, injection of triamcinolone and vitrectomy. However, these treatments do not cure diabetic retinopathy and often have complications. For example, laser surgery may cause loss of retinal tissue. Triamcinolone may cause a marked increase in vision. Vitrectomy replaces the cloudy vitreous solution and replaces it with saline; however, surgical intervention may not be helpful in all patients. Thus, the disclosed PDE 1 inhibitors, either alone or in combination with other therapeutic agents, such as those disclosed here, may an alternative for the treatment of diabetic retinopathy.

In another embodiment, the PDE 1 Inhibitors are compounds of Formula Ia selected from the following:

Compound 1

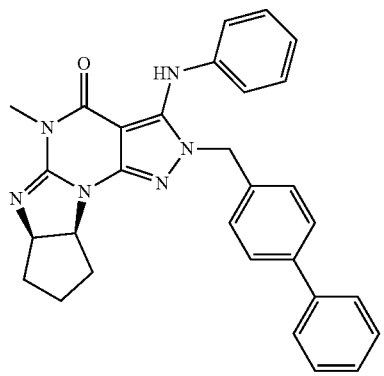 [SMILES: CN1C(=O)c2c(nn(Cc3ccc(-c4ccccn4)cc3)c2Nc2ccccc2)N2C1=N[C@@H]1CCC[C@@H]12]

Compound 2

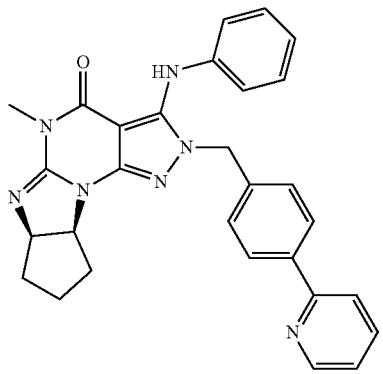

Alternatively, an effective amount of a PDE-1 inhibitor may be synergistically combined with an effective amount of a prostaglandin or a prostaglandin analog for effectively increasing eyelash growth.

Methods of Treatment

The invention provides methods of treatment in a human or animal patient suffering from glaucoma or elevated intraocular pressure or intraocular hypertension that may be ameliorated by said enhancement comprising administering an effective amount of a PDE 1 inhibitor, e.g., a PDE 1 Inhibitor as hereinbefore described, for example a Compound of Formula I, Ia, II, III, IV, V, VIIa, VIIb, VIIIa, VIIIb, IXa, IXb, or any of Formulae 1.2-1.17, 2.1-2.9, 3.2-3.22, 4.1-4.16, 5.1-5.6 to a human or animal patient, preferably a human, in need thereof. PDE 1 inhibitors of said method also include Compound of Formula X or XI or any of 6.1 or 7.1-7.12.

PDE 1 Inhibitors may be used in the foregoing methods of treatment or prophylaxis as a sole therapeutic agent, but may also be used in combination or for co-administration with other active agents, for example in conjunction with other intraocular pressure lowering agents. Thus, the invention further comprises a method of treating disorders that may be ameliorated by enhancement of progesterone signaling comprising administering simultaneously, sequentially, or contemporaneously administering therapeutically effective amounts of (i) a PDE 1 Inhibitor, e.g., of Formula I, Ia, II, III, IV, V, VIIa, VIIb, VIIIa, VIIIb, IXa or IXb, or any of Formulae 1.2-1.17, 2.1-2.9, or 3.2-3.22, 4.1-4.16, 5.1-5.6;

(ii) an intraocular pressure lowering agent to a patient in need thereof.

The invention also comprises a method of treating glaucoma or glaucoma-like conditions comprising administering simultaneously, sequentially, or contemporaneously administering therapeutically effective amounts of sss (i) a PDE 1 Inhibitor, e.g., of Formula X or XI or any of 6.1 or 7.1-7.12;

(ii) an intraocular pressure lowering agent.

to a patient in need thereof.

The invention also comprises a method of treating glaucoma or elevated intraocular pressure comprising administering simultaneously, sequentially, or contemporaneously administering therapeutically effective amounts of sss (i) a PDE 1 Inhibitor, e.g., of Formula XII-XIII or any of 8.1-8.30

(ii) an intraocular pressure lowering agent.

to a patient in need thereof.

The present invention also provides (i) a PDE 1 Inhibitor for use in the treatment of glaucoma or glaucoma-like conditions, as hereinbefore set forth, or in a method of treatment as hereinbefore set forth;

(ii) the use of a PDE 1 Inhibitor in the manufacture of a medicament for treating a glaucoma or glaucoma-like conditions, or manufacture of a medicament for use in a method of treatment as hereinbefore set forth; and (iii) a pharmaceutical composition comprising a PDE 1 Inhibitor in combination or association with a pharmaceutically acceptable diluent or carrier for use in the treatment of a glaucoma or elevated intraocular pressure as hereinbefore set forth, or for use in a method of treatment as hereinbefore set forth.

The words "treatment" and "treating" are to be understood accordingly as embracing prophylaxis and treatment or amelioration of any of the symptoms of disease as well as treatment of the cause of the disease.

Dosages employed in practicing the present invention will of course vary depending, e.g. on the particular disease or condition to be treated, the particular PDE 1 Inhibitor used, the mode of administration, and the therapy desired. PDE 1 Inhibitors may be administered by any suitable route, including orally, parenterally, transdermally, or by inhalation, but are preferably administered topically to the eyes. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a PDE 1 Inhibitor, together with a pharmaceutically acceptable diluent or carrier therefor.

Pharmaceutical compositions comprising PDE 1 Inhibitors may be prepared using conventional diluents or excipients and techniques known in the galenic art. Thus oral dosage forms may include tablets, capsules, creams, ointments, solutions, suspensions and the like. In addition, ophthalmic disorders other than glaucoma may be treated by the compositions disclosed.

EXAMPLE I

1. Measurement of PDE1B inhibition in Vitro Using IMAP Phosphodiesterase Assay Kit Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

2. Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A method of treatment of glaucoma or elevated intraocular pressure comprising topically administering an effective amount of a PDE 1 inhibitor, or a combination of a PDE 1 inhibitor and an intraocular pressure-lowering agent, to the eye of a patient in need thereof wherein the PDE 1 inhibitor is the following compound:

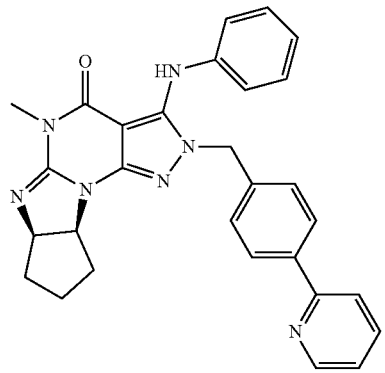

in free or salt form.

2. The method according to claim 1, wherein a combination of the PDE1 inhibitor and an intraocular pressure-lowering agent is administered to the patient.

3. The method according to claim 2, wherein the intraocular pressure-lowering agent is an alpha adrenergic agonist, a beta-adrenergic antagonist, a prostaglandin or prostaglandin analog or a muscarinic agonist, a sympathomimetic, a miotic agent, a carbonic anhydrase inhibitor, a prostanoid, physostigmine, bimatoprost, brimonidine tartrate, or brimonidine tartrate/timolol maleate, or a combination thereof.

4. The method according to claim 2, wherein the prostaglandin is travoprost, latanoprost, bimatroprost, unoprostone, or unoprostone isopropyl.

5. The method according to claim 2, wherein the alpha adrenergic agonist is brimonidine, apraclonidine or dipivefrin.

6. The method according to claim 2, wherein the muscarinic agonist is pilocarpine.

* * * * *

UNITED STATES PATENT AND TRADEMARK OFFICE
CERTIFICATE OF CORRECTION

| | | |
|---|---|---|
| PATENT NO. | : 11,464,781 B2 | Page 1 of 1 |
| APPLICATION NO. | : 13/203365 | |
| DATED | : October 11, 2022 | |
| INVENTOR(S) | : Davis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1331 days.

Signed and Sealed this
Twenty-first Day of January, 2025

Coke Morgan Stewart
*Acting Director of the United States Patent and Trademark Office*